(12) United States Patent
Boenitz-Dulat et al.

(10) Patent No.: US 7,781,196 B2
(45) Date of Patent: Aug. 24, 2010

(54) THERMOSTABLE MUTANTS OF PYRROLOQUINOLINE QUINONE DEPENDENT GLUCOSE DEHYDROGENASE

(75) Inventors: Mara Boenitz-Dulat, Tutzing (DE); Peter Kratzsch, Penzberg (DE); Rainer Schmuck, Benediktbeuern (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 693 days.

(21) Appl. No.: 11/665,437

(22) PCT Filed: Oct. 14, 2005

(86) PCT No.: PCT/EP2005/011077

§ 371 (c)(1),
(2), (4) Date: Apr. 13, 2007

(87) PCT Pub. No.: WO2006/040172

PCT Pub. Date: Apr. 20, 2006

(65) Prior Publication Data

US 2009/0305316 A1 Dec. 10, 2009

(30) Foreign Application Priority Data

Oct. 15, 2004 (EP) ................. 04024593

(51) Int. Cl.
*C12N 9/04* (2006.01)
*C12N 1/20* (2006.01)
*C12N 15/00* (2006.01)
*C12P 21/04* (2006.01)
*C12M 1/00* (2006.01)
*C12Q 1/00* (2006.01)
*C07H 21/04* (2006.01)
*C12Q 1/68* (2006.01)

(52) U.S. Cl. ............... 435/190; 435/4; 435/6; 435/69.1; 435/71.1; 435/252.3; 435/320.1; 435/440; 536/23.2; 205/777.5; 204/403.01; 204/403.1

(58) Field of Classification Search ................ None
See application file for complete search history.

(56) References Cited

U.S. PATENT DOCUMENTS

| 5,484,708 A | 1/1996 | Hoenes et al. |
| 5,997,817 A | 12/1999 | Crismore et al. |
| 6,057,120 A | 5/2000 | Heindl et al. |
| 6,103,509 A | 8/2000 | Sode |

FOREIGN PATENT DOCUMENTS

| EP | 0 620 283 B1 | 9/1998 |
| EP | 1 167 519 A1 | 1/2002 |
| EP | 1 176 202 A1 | 1/2002 |
| EP | 1 367 120 A2 | 12/2003 |
| JP | 11-243949 | 9/1999 |
| JP | 2004-173538 | 6/2004 |
| WO | WO 88/09373 | 12/1988 |
| WO | WO 02/34919 A1 | 5/2002 |
| WO | WO 2006/040172 A1 | 4/2006 |

OTHER PUBLICATIONS

UniProtKB/TrEMBL Database—Accession Q82JL8, 2003.*
Anthony, Christopher; "Quinoprotein-catalysed reactions," Biochem. J. 320 (1996) 697-711.
Anthony, Christopher et al., "The structure and function of PQQ-containing quinoproteins," Curr. Science 72 (1997) 716-727.
Anthony, Christopher et al., "The structure and function of the PQQ-containing quinoprotein dehydrogenases," Prog. Biophys. Mol. Biol. 69 (1998) 1-21.
Anthony, C., "The pyrroloquinoline quinone (PQQ)-containing quinoprotein dehydrogenases," Biochem. Soc. Trans. 26 (1998) 413-417.
Anthony, Christopher, "The Pyrroloquinoline Quinone (PQQ)-Containing Dehydrogenases," Adv. in Phot. and Resp. , Chapter 10, 15 (2004) 203-225.
Ausubel, Frederick M. et al., "Current protocols in molecular biology" vol. 1, (1994), Wiley Verlag.
Cleton-Jansen, Anne-Marie et al., "Cloning of the Genes Encoding the Two Different Glucose Dehydrogenases from *Acinetobacter calcoaceticus*," Antonie Van Leeuwenhoek 56 (1989) 73-79.
Cleton-Jansen, Anne-Marie et al., "Cloning of the Gene Encoding Quinoprotein Glucose Dehydrogenase from *Acinetobacter calcoaceticus*: Evidence for the Presence of a Second Enzyme," J. Bacteriol. 170 (1988) 2121-2125.
Cleton-Jansen, Anne-Marie et al., "Cloning, characterization and DNA sequencing of the gene encoding the $M_r$ 50 000 quinoprotein glucose dehydrogenase from *Acinetobacter calcoaceticus*," Mol. Genet 217 (1989) 430-436.
D'Costa, E.J., et al., " uinoprotein Glucose Dehydrogenase and its Application in an Amperometric Glucose Sensor," Biosensors 2 (1986) 71-87.
Database Accession No. ADP90774—XP002308323, Database Geneseq.
Dokter, Paul, et al., "Purification and characterization of quinoprotein glucose dehydrogenase from *Acinetobacter calcoaceticus* L.M.D. 79.41," Biochem J. 239 (1986) 163-167.
Dokter, Paul et al., "Cytochrome *b*-562 from *Acinetobacter calcoaceticus* L.M.D. 79.41," Biochem J. 254 (1988) 131-138.
Dokter, P., et al., "The in vivo and in vitro substrate specificity of quinoprotein glucose dehydrogenase of *Acinetobacter calcoaceticus* LMD79.41," FEMS Microbiology Letters 43 (1987) 195-200.

(Continued)

Primary Examiner—Yong D Pak
(74) Attorney, Agent, or Firm—Barnes & Thornburg LLP

(57) ABSTRACT

The present invention relates to a mutant protein of PQQ-dependent s-GDH characterized in that in at least one of the positions 122 and 124 the amino acid lysine is present, wherein these positions correspond to the amino acid positions known from the *A. calcoaceticus* s-GDH wild-type sequence (SEQ ID NO: 2), it also discloses genes encoding such mutant s-GDH, and different applications of these s-GDH mutants, particularly for determining the concentration of glucose in a sample.

23 Claims, 4 Drawing Sheets

OTHER PUBLICATIONS

Duine, J.A., "Energy generation and the glucose dehydrogenase pathway in *Acinetobacter*," The Biology of *Acinetobacter*(1991) 295-312, New York, Plenum Press.

Duine, J.A., "The importance of natural diversity in redox proteins for achieving cofactor-electrode-directed electron transfer," Biosensors & Bioelectronics 10 (1995) 17-23.

Duine, Johannis A., "Quinoproteins: enzymes containing the quinonoid cofactor pyrroloquinoline quinone, topaquinone or tryptophan-tryptophan quinone," Eur. J. Biochem. 200 (1991) 271-284.

Feng, Da-Fei et al., "Progressive Sequence Alignment as a Prerequisite to Correct Phylogenetic Trees," J. Mol. Evol. 25 (1987) 351-360.

Frampton, James E. et al., "Icodextrin: A Review of its Use in Peritoneal Dialysis," Drugs 63 (2003) 2079-2105.

Goodwin, Pat M., et al., "The Biochemistry, Physiology and Genetics of PQQ and PQQ-Containing Enzymes," Adv. Microbiol. Physiol. 40 (1998) 1-80.

Hill, David E., et al., Methods in Enzymology, vol. 155 (1987) 558-568.

Igarashi, Satoshi et al., "Construction and Characterization of Mutant Water-Soluble PQQ-Glucose Dehydrogenases with Altered $K_m$ Values—Site-Directed Mutagenesis Studies on the Putative Active Site," Biochemical and Biophysical Research Communications, 264 (1999) 820-824.

Kaufmann, Norbert et al., "Development and evaluation of a new system for determining glucose from fresh capillary blood and heparinised venous blood," Glucotrend (1997) 1-16, Mannheim, Boehringer Mannheim GmbH.

Kim, Chul Hong, et al., "Cloning and Expression of Pyrroloquinoline Quinone (PQQ) Genes from a Phosphate-Solubilizing Bacterium *Enterobacter intermedium*," Current Microbiology 47 (2003) 457-461.

Laurinavicius, V., et al., "Oxygen Insensitive Glucose Biosensor Based on PQQ-Dependent Glucose Dehydrogenase," Analytical Letters 32 (1999) 299-316.

Laurinavicius, Valdas et al., "A Novel Application of Heterocyclic Compounds for Biosensors Based on *NAD, FAD*, and *PQQ* Dependent Oxidoreductases," Monatshefte fur Chemie 130 (1999) 1269-1281.

Laurinavicius, V. et al., "Comparative characterization of soluble and membrane-bound PQQ-glucose dehydrogenases," Biologija (2003) Nr. 2, 31-34.

Leung, David W. et al., "A Method For Random Mutagenesis Of A Defined DNA Segment Using A Modified Polymerase Chain Reaction," Technique 1 (1989) 11-15.

Matsushita, Kazunobu et al., "Bacterial quinoproteins glucose dehydrogenase and alcohol dehydrogenase," Principles and Applications of Quinoproteins (1993) 47-63, New York, Marcel Dekker.

Matsushita, Kazunobu et al., "Quinoprotein D-glucose dehydrogenase in *Acinetobacter calcoaceticus* LMD 79:41: Purification and characterization of the membrane-bound enzyme distinct from the soluble enzyme," Antonie Van Leeuwenhoek 56 (1989) 63-72.

Matsushita, Kazunobu et al., "Quinoprotein D-Glucose Dehydrogenase of the *Acinetobacter calcoaceticus* Respiratory Chain: Membrane-Bound and Soluble Forms Are Different Molecular Species," Biochemistry 28 (1989) 6276-6280.

Matsushita, Kazunobu et al., "Soluble and Membrane-bound Quinoprotein D-Glucose Dehydrogenase of the *Acinetobacter calcoaceticus*: The Binding Process of PQQ to the Apoenzymes," Bioscience Biotech. & Biochem. 59 (1995) 1548-1555.

Olsthooorn, Arjen J.J. et al., "Production, Characterization, and Reconstitution of Recombinant Quinoprotein Glucose Dehydrogenase (Soluble Type; EC 1.1.99.17) Apoenzyme of *Acinetobacter calcoaceticus*," Archives of Biochemistry and Biophysics 336 (1996) 42-48.

Olsthooorn, Arjen J.J. et al., "On the Mechanism and Specificity of Soluble, Quinoprotein Glucose Dehydrogenase in the Oxidation of Aldose Sugars," Biochemistry 37 (1998) 13854-13861.

Oubrie, Arthur, "Structure and mechanism of soluble glucose dehydrogenase and other PQQ-dependent enzymes," Biochimica et Biophysica Acta 1647 (2003) 143-151.

Oubrie, Arthur et al., "Structural requirements of pyrroloquinoline quinone dependent enzymatic reactions," Protein Science 9 (2000) 1265-1273.

Oubrie, Arthur et al., "Structure and mechanism of soluble quinoprotein glucose dehydrogenase," The Embo Journal 18 (1999) 5187-5194.

Oubrie, Arthur et al., "The 1.7 å Crystal Structure of the Apo Form of the Soluble Quinoprotein Glucose Dehydrogenase from *Acinetobacter calcoaceticus* Reveals a Novel Internal Conserved Sequence Repeat," J. Mol. Biol. 289 (1999) 319-333.

Oubrie, Arthur et al., "Active-site structure of the soluble quinoprotein glucose dehydrogenase complexed with methylhydrazine: A covalent cofactor-inhibitor complex," Proc. Natl. Acad. Sci, U.S.A. 96 (1999) 11787-11791.

Reddy, Swarnalatha Y. et al., "Mechanism of Glucose Oxidation by Quinoprotein Soluble Glucose Dehydrogenase: Insights from Molecular Dynamics Studies," J. Am. Chem. Soc. 126 (2004) 2431-2438.

Wens, Robert et al., Peritoneal Dialysis International, vol. 18 (1998) 603-609.

Yamada, Mamoru et al., *Escherichia coli* PQQ-containing quinoprotein glucose dehydrogenase: its structure comparison with other quinoproteins, Biochim. Biophys. Acta 1647 (2003) 185-192.

Ye, Ling et al., "High Current Density 'Wired' Quinoprotein Glucose Dehydrogenase Electrode," Anal. Chem. 65 (1993) 238-241.

\* cited by examiner

Fig. 1

Amino acid sequences of A. calcoaceticus (top) and
A. baumannii (bottom)

```
  1 DVPLTPSQFAKAKSENFDKKVILSNLNKPHALLWGPDNQIWLTERATGKI  50
    |:||||.|||||.|||||||||||||||||||||||||||||||||||||
  1 DIPLTPAQFAKAKTENFDKKVILSNLNKPHALLWGPDNQIWLTERATGKI  50

51 LRVNPESGSVKTVFQVPEIVNDADGQNGLLGFAFHPDFKNNPYIYISGTF 100
    |||||  |||  ||||||||||||.||||||||||||||-|||||||||
 51 LRVNPVSGSAKTVFQVPEIVSDADGQNGLLGFAFHPDFKHNPYIYISGTF 100

101 KNPKSTDKELPNQTIIRRYTYNKSTDTLEKPVDLLAGLPSSKDHQSGRLV 150
    ||||||||||||||||||||||||.|||  |||:||:|||||||||||||
101 KNPKSTDKELPNQTIIRRYTYNKTTDTFEKPIDLIAGLPSSKDHQSGRLV 150

151 IGPDQKIYYTIGDQGRNQLAYLFLPNQAQHTPTQQELNGKDYHTYMGKVL 200
    |||||||||||||||||||||||| ||||||||||||| |||||||||||
151 IGPDQKIYYTIGDQGRNQLAYLFLSNQAQHTPTQQELNSKDYHTYMGKVL 200

201 RLNLDGSIPKDNPSFNGVVSHIYTLGHRNPQGLAFTPNGKLLQSEQGPNS 250
    ||:||||||||||||||||||||||||||||||||| |||||||||||||
201 RLNLDGSIPKDNPSFNGVVSHIYTLGHRNPQGLAFAPNGKLLQSEQGPNS 250

251 DDEINLIVKGGNYGWPNVAGYKDDSGYAYANYSAAANKS.IKDLAQNGVK 299
    ||||||:.|||||||||||||||||||||||||||| ||| |||||||:|
251 DDEINLVLKGGNYGWPNVAGYKDDSGYAYANYSAATNKSQIKDLAQNGIK 300

300 VAAGVPVTKESEWTGKNFVPPLKTLYTVQDTYNYNDPTCGEMTYICWPTV 349
    || |||||||||||||||||||||||||||||||||||||||| |||||||
301 VATGVPVTKESEWTGKNFVPPLKTLYTVQDTYNYNDPTCGEMAYICWPTV 350

350 APSSAYVYKGGKKAITGWENTLLVPSLKRGVIFRIKLDPTYSTTYDDAVP 399
    ||||||||  ||||||  |||||||||||||||||||||||||||  |||:|
351 APSSAYVYTGGKKAIPGWENTLLVPSLKRGVIFRIKLDPTYSTTLDDAIP 400

400 MFKSNNRYRDVIASPDGNVLYVLTDTAGNVQKDDGSVTNTLENPGSLIKF 449
    |||||||||||||||:||||||||||||||||||||||||-||||||||||
401 MFKSNNRYRDVIASPEGNTLYVLTDTAGNVQKDDGSVTHTLENPGSLIKF 450

450 TYKAK 454
    || |
451 TYNGK 455
```

Schematic diagram of the plasmide with gene for s-GDH (pACSGDH)

Fig. 3a

Sequence vector pACSGDH

```
cactaactga ttacgcaccg catgtaaccg ttttcaatct gtgagtaaat tcacagttta   60
ttaacattgt gatagctatg atgacaacgt ttgtcgcact gtaactaacg tgtaacagtt  120
agttgtcagt tttgctgggg tatttcgctt ataaaaaccg ttatcacaat atcccgcgac  180
taccggacaa aaataaagag ttgaataaga gcttatccca ttagggctat tttacttgcc  240
attttggacc tgggcagtgc tcgccaaaac gcgttagcgt tttgaacgcg ctagcgcgg   300
cccgaagggc gagcgtagcg agtcaaacct cacgtactac gtgtacgctc cggtttttgc  360
gcgctgtccg tgtccaaact gctgcgccaa taacgcctgg tgggataggc tctaaatacg  420
cttcggcgtt cagtaacacg cgttaacgtg ctgaacagcc gggcatttt ttacgctata   480
ccctacataa taaaaccgga gctaccatga ataagaaggt actgacccct tctgccgtga  540
tggcaagtct gttattcggc gcgcacgcgc atgccgccga tgttcctcta actccatctc  600
aatttgctaa agcgaaatca gagaactttg acaagaaagt tattctatct aatctaaata  660
agccgcacgc gttgttatgg ggaccagata atcaaatttg gttaactgag cgagcaacag  720
gtaagattct aagagttaat ccagagtcgg gtagtgtaaa aacagttttt caggtaccag  780
agattgtcaa tgatgctgat gggcagaatg gtttattagc ttttgccttc catcctgatt  840
ttaaaaataa tccttatatc tatatttcag gtacatttaa aaatccgaaa tctacagata  900
aagaattacc gaaccaaacg attattcgtc gttataccta taataaatca acagatacgc  960
tcgagaagcc agtcgattta ttagcaggat taccttcatc aaaagaccat cagtcaggtc 1020
gtcttgtcat tgggccagat caaaagattt attatacgat tggtgaccaa gggcgtaacc 1080
agcttgctta tttgttcttg ccaaatcaag cacaacatac gccaactcaa caagaactga 1140
atggtaaaga ctatcacacc tatatgggta aagtactacg cttaaatctt gatggaagta 1200
ttccaaagga taatccaagt tttaacgggg tggttagcca tatttataca cttgacatc  1260
gtaatccgca gggcttagca ttcactccaa atggtaaatt attgcagtct gaacaaggcc 1320
caaactctga cgatgaaatt aacctcattg tcaaaggtgg caattatgct tggccgaatg 1380
tagcaggtta taaagatgat agtggctatg cttatgcaaa ttattcagca gcagccaata 1440
agtcaattaa ggatttagct caaatggag taaaagtagc cgcagggtc cctgtgacga 1500
aagaatctga atggactggt aaaaactttg tcccaccatt aaaaactta tataccgttc  1560
aagataccta caactataac gatccaactt gtggagagat gacctacatt tgctggccaa 1620
cagttgcacc gtcatctgcc tatgtctata agggcggtaa aaaagcaatt actggttggg 1680
aaaatacatt attggttcca tctttaaaac gtggtgtcat tttccgtatt aagttagatc  1740
caacttatag cactactat gatgacgctg taccgatgtt taagagcaac aaccgttatc  1800
gtgatgtgat tgcaagtcca gatgggaatg tcttatatgt attaactgat actgccggaa  1860
atgtccaaaa agatgatgga tcagtaacaa atacattaga aaaccagga tctctcatta  1920
agttcaccta taaggctaag taatacagtc gcattaaaaa accgatctat aaagatcggt  1980
tttttagtt ttagaaaaga attcactggc cgtcgtttta caacgtcgtg actgggaaaa  2040
ccctggcgtt acccaactta atcgccttgc agcacatccc ctttcgcca gctggcgtaa  2100
tagcgaagag gcccgcaccg atcgccttc ccaacagttg cgcagcctga atggcgaatg  2160
gcgcctgatg cggtatttc tccttacgca tctgtgcggt atttcacacc gcatatggtg  2220
cactctcagt acaatctgct ctgatgccgc atagttaagc cagccccgac acccgccaac  2280
acccgctgac gcgccctgac gggcttgtct gctcccggca tccgcttaca gacaagctgt  2340
gaccgtctcc gggagctgca tgtgtcagag gttttcaccg tcatcaccga aacgcgcgag  2400
acgaaagggc ctcgtgatac gcctattttt ataggttaat gtcatgataa taatggttc   2460
ttagacgtca ggtggcactt ttcggggaaa tgtgcgcgga acccctattt gtttatttt  2520
ctaaatacat tcaaatatgt atccgctcat gagacaataa ccctgataaa tgcttcaata  2580
atattgaaaa aggaagagta tgagtattca acatttccgt gtcgccctta ttcccttttt  2640
tgcggcattt tgccttcctg tttttgctca cccagaaacg ctggtgaaag taaaagatgc  2700
tgaagatcag ttgggtgcac gagtgggtta catcgaactg gatctcaaca gcggtaagat  2760
ccttgagagt tttcgccccg aagaacgttt tccaatgatg agcactttta aagttctgct  2820
atgtggcgcg gtattatccc gtattgacgc cgggcaagag caactcggtc gccgcataca  2880
```

Fig. 3b

```
ctattctcag aatgacttgg ttgagtactc accagtcaca gaaaagcatc ttacggatgg 2940
catgacagta agagaattat gcagtgctgc cataaccatg agtgataaca ctgcggccaa 3000
cttacttctg acaacgatcg gaggaccgaa ggagctaacc gcttttttgc acaacatggg 3060
ggatcatgta actcgccttg atcgttggga accggagctg aatgaagcca taccaaacga 3120
cgagcgtgac accacgatgc ctgtagcaat ggcaacaacg ttgcgcaaac tattaactgg 3180
cgaactactt actctagctt cccggcaaca attaatagac tggatggagg cggataaagt 3240
tgcaggacca cttctgcgct cggcccttcc ggctggctgg tttattgctg ataaatctgg 3300
agccggtgag cgtgggtctc gcggtatcat tgcagcactg gggccagatg gtaagccctc 3360
ccgtatcgta gttatctaca cgacggggag tcaggcaact atggatgaac gaaatagaca 3420
gatcgctgag ataggtgcct cactgattaa gcattggtaa ctgtcagacc aagtttactc 3480
atatatactt tagattgatt taaaacttca tttttaattt aaaaggatct aggtgaagat 3540
cctttttgat aatctcatga ccaaaatccc ttaacgtgag ttttcgttcc actgagcgtc 3600
agaccccgta gaaaagatca aaggatcttc ttgagatcct ttttttctgc gcgtaatctg 3660
ctgcttgcaa acaaaaaaac caccgctacc agcggtggtt tgtttgccgg atcaagagct 3720
accaactctt tttccgaagg taactggctt cagcagagcg cagataccaa atactgtcct 3780
tctagtgtag ccgtagttag gccaccactt caagaactct gtagcaccgc ctacatacct 3840
cgctctgcta atcctgttac cagtggctgc tgccagtggc gataagtcgt gtcttaccgg 3900
gttggactca agacgatagt taccggataa ggcgcagcgg tcgggctgaa cggggggttc 3960
gtgcacacag cccagcttgg agcgaacgac ctacaccgaa ctgagatacc tacagcgtga 4020
gctatgagaa agcgccacgc ttcccgaagg gagaaaggcg gacaggtatc cggtaagcgg 4080
cagggtcgga acaggagagc gcacgaggga gcttccaggg gaaacgcct ggtatcttta 4140
tagtcctgtc gggtttcgcc acctctgact tgagcgtcga ttttgtgat gctcgtcagg 4200
ggggcggagc ctatggaaaa acgccagcaa cgcggccttt ttacggttcc tggccttttg 4260
ctggcctttt gctcacatgt tctttcctgc gttatcccct gattctgtgg ataaccgtat 4320
taccgccttt gagtgagctg ataccgctcg ccgcagccga cgacggggc ccg         4373
```

THERMOSTABLE MUTANTS OF PYRROLOQUINOLINE QUINONE DEPENDENT GLUCOSE DEHYDROGENASE

CROSS-REFERENCE TO RELATED APPLICATIONS

This application is a U.S. national counterpart application of international application serial no. PCT/EP2005/011077 filed Oct. 14, 2005, which claims priority to European application serial no. 04024593.8 filed Oct. 15, 2004.

The present invention relates to a mutant protein of PQQ-dependent s-GDH characterized in that in at least one of the positions 122 and 124 the amino acid lysine is present, wherein these positions correspond to the amino acid positions known from the *A. calcoaceticus* s-GDH wild-type sequence (SEQ ID NO: 2), it also discloses genes encoding such mutant s-GDH, and different applications of these s-GDH mutants, particularly for determining the concentration of glucose in a sample.

FIELD OF THE INVENTION

The determination of blood glucose concentration is extremely important in clinical diagnosis and in the management of diabetes. Approximately 150 million people worldwide suffer from the chronic disease diabetes mellitus, a figure that may double by 2025 according to the WHO. Although diabetes is readily diagnosed and treated, successful long-term management requires low-cost diagnostic tools that rapidly and accurately report blood glucose concentrations. PQQ-dependent glucose dehydrogenases (EC 1.1.5.2) catalyze a reaction in which glucose is oxidized to gluconolactone. Consequently, this type of enzyme is used in measuring blood sugar. One of these tools is a diagnostic strip based on the soluble glucose dehydrogenase (s-GlucDOR, EC 1.1.5.2), a pyrroloquinoline quinone-containing enzyme originally derived from *Acinetobacter calcoaceticus*.

Quinoproteins use quinone as cofactor to oxidize alcohols, amines and aldoses to their corresponding lactones, aldehydes and aldolic acids (Duine, J. A., Energy generation and the glucose dehydrogenase pathway in *Acinetobacter* in "The Biology of *Acinetobacter*" (1991) 295-312, New York, Plenum Press; Duine, J. A., Eur. J. Biochem. 200 (1991) 271-284; Davidson, V. L., in "Principles and applications of quinoproteins" (1993), the whole book, New York, Marcel Dekker; Anthony, C., Biochem. J. 320 (1996) 697-711; Anthony, C. and Ghosh, M., Current Science 72 (1997) 716-727; Anthony, C., Biochem. Soc. Trans. 26 (1998) 413-417; Anthony, C. and Ghosh, M., Prog. Biophys. Mol. Biol. 69 (1998) 1-21. Among quinoproteins, those containing the non-covalently bound cofactor 2,7,9-tricarboxy-1H-pyrrolo [2,3-f]quinoline-4,5-dione (PQQ) constitute the largest sub-group (Duine 1991, supra). All bacterial quinone glucose dehydrogenases known so far belong to this sub-group with PQQ as cofactor (Anthony and Ghosh 1997 supra; Goodwin, P. M. and Anthony, C., Adv. Microbiol. Physiol. 40 (1998) 1-80; Anthony, C., Adv. in Phot. and Resp. 15 (2004) 203-225).

Two types of PQQ-dependent glucose dehydrogenase (EC 1.1.5.2) have been characterized in bacteria: One is membrane-bound (m-GDH); the other is soluble (s-GDH). Both types do not share any significant sequence homology (Cleton-Jansen, A. M., et al., Mol. Gen. Genet. 217 (1989) 430-436; Cleton-Jansen, A. M., et al., Antonie Van Leeuwenhoek 56 (1989) 73-79; Oubrie, A., et al., Proc. Natl. Acad. Sci. U.S.A. 96 (1999) 11787-11791). They are also different regarding both their kinetic as well as their immunological properties (Matsushita, K., et al., Bioscience Biotechnol. Biochem. 59 (1995) 1548-1555). The m-GDHs are widespread in Gram-negative bacteria, s-GDHs, however, have been found only in the periplasmatic space of *Acinetobacter* strains, like *A. calcoaceticus* (Duine, J. A., 1991a; Cleton-Jansen, A. M. et al., J. Bacteriol. 170 (1988) 2121-2125; Matsushita and Adachi, 1993) and *A. baumannii* (JP 11243949).

Through searching sequence databases, two sequences homologous to the full-length *A. calcoaceticus* s-GDH have been identified in *E. coli* K-12 and *Synechocystis* sp. Additionally, two incomplete sequences homologous to *A. calcoaceticus* s-GDH were also found in the genome of *P. aeruginosa* and *Bordetella pertussis* (Oubrie et al. 1999 a, b, c) and *Enterobacter intermedium* (Kim, C. H. et al., Current Microbiol. 47 (2003) 457-461), respectively. The deduced amino acid sequences of these four uncharacterized proteins are closely related to *A. calcoaceticus* s-GDH with many residues in the putative active site absolutely conserved. These homologous proteins are likely to have a similar structure and to catalyze similar PQQ-dependent reactions (Oubrie et al., 1999 a, b, c; Oubrie A., Biochim. Biophys. Acta 1647 (2003) 143-151; Reddy, S., and Bruice, T. C., J. Am. Chem. Soc. 126 (2004) 2431-2438; Yamada, M. et al., Biochim. Biophys. Acta 1647 (2003) 185-192).

Bacterial s-GDHs and m-GDHs have been found to possess quite different sequences and different substrate specificity. For example, *A. calcoaceticus* contains two different PQQ-dependent glucose dehydrogenases, one designated m-GDH which is active in vivo, and the other designated s-GDH for which only in vitro activity can be shown. Cleton-Jansen et al., 1988; 1989 a, b cloned the genes coding for the two GDH enzymes and determined the DNA sequences of both of these GDH genes. There is no obvious homology between m-GDH and s-GDH corroborating the fact that m-GDH and s-GDH represent two completely different molecules (Laurinavicius, V., et al, Biologija (2003) 31-34).

The gene of s-GDH from *A. calcoaceticus* has been cloned in *E. coli*. After being produced in the cell, the s-GDH is translocated through the cytoplasmic membrane into the periplasmic space (Duine, J. A., Energy generation and the glucose dehydrogenase pathway in *Acinetobacter* in "The Biology of *Acinetobacter*" (1991) 295-312, New York, Plenum Press; Matsushita, K. and Adachi, O., Bacterial quinoproteins glucose dehydrogenase and alcohol dehydrogenase in "Principles and applications of Quinoproteins" (1993) 47-63, New York, Marcel Dekker). Like the native s-GDH from *A. calcoaceticus*, recombinant s-GDH expressed in *E. coli* is a homodimer, with one PQQ molecule and three calcium ions per monomer (Dokter, P. et al., Biochem. J. 239 (1986) 163-167; Dokter, P. et al., FEMS Microbiol. Lett. 43 (1987) 195-200; Dokter, P. et al., Biochem. J. 254 (1988) 131-138; Olsthoorn, A. J. and Duine, J. A., Arch. Biochem. Biophys. 336 (1996) 42-48; Oubrie, A., et al., J. Mol. Biol. 289 (1999) 319-333; Oubrie, A., et al., Proc. Natl. Acad. Sci. U.S.A 96 (1999) 11787-11791; Oubrie, A., et al., Embo J. 18 (1999) 5187-5194). s-GDH oxidizes a wide range of mono- and disaccharides to the corresponding ketones which further hydrolyze to the aldonic acids, and it is also able to donate electrons to PMS (phenazine metosulfate), DCPIP (2,6-dichloro-phenolindophenol), WB (Wurster's blue) and short-chain ubiquinones such as ubiquinone Q1 and ubiquinone Q2 (Matsushita, K., et al., Biochem. 28 (1989) 6276-6280; Matsushita, K., et al., Antonie Van Leeuwenhoek 56 (1989) 63-72), several artificial electron acceptors such as N-methylphenazonium methyl sulfate (Olsthoorn, A. J. and Duine, J. A., Arch. Biochem. Biophys. 336 (1996) 42-48; Olsthoorn, A. J. and Duine, J. A., Biochem. 37 (1998) 13854-13861) and electro conducting polymers (Ye, L., et al., Anal. Chem. 65 (1993) 238-241). In view of s-GDH's high specific activity towards glucose (Olsthoorn, A. J. and Duine, J. A., (1996) supra) and its broad artificial electron acceptor specificity, the enzyme is well suited for analytical applications, particularly for being used in (bio-)sensor or test strips for glucose determination in diagnostic applications (Kaufmann, N. et al., Development and evaluation of a new system for determining glucose from fresh capillary blood and heparinized blood in "Glucotrend" (1997) 1-16, Boehringer Mannheim GmbH; Malinauskas, A.; et al., Sensors and Actuators, B: Chemical 100 (2004) 395-402).

Glucose oxidation can be catalyzed by at least three quite distinct groups of enzymes, i.e., by NAD/P-dependent glucose dehydrogenases, by flavoprotein glucose oxidases or by quinoprotein GDHs (Duine, J. A., Biosens. Bioelectronics 10 (1995) 17-23). A rather slow autooxidation of reduced s-GDH has been observed, demonstrating that oxygen is a very poor electron acceptor for s-GDH (Olsthoorn and Duine, 1996). s-GDH can efficiently donate electrons from the reduced quinone to mediators such as PMS, DCPIP, WB and short-chain ubiquinones such as Q1 and Q2, but it can not efficiently donate electrons directly to oxygen.

Traditional test strips and sensors for monitoring glucose level in blood, serum and urine e.g. from diabetic patients use glucose oxidase. The performance of the enzyme is dependent of the oxygen concentration. Glucose measurements at different altitudes with different oxygen concentrations in the air may lead to false results. The major advantage of PQQ-dependent glucose dehydrogenases is their independence from oxygen. This important feature is e.g., discussed in U.S. Pat. No. 6,103,509, in which some features of membrane-bound GDH have been investigated.

An important contribution to the field has been the use of s-GDH together with appropriate mediators. Assay methods and test strip devices based on s-GDH are disclosed in detail in U.S. Pat. No. 5,484,708. This patent also contains detailed information on the set-up of assays and the production of s-GDH-based test strips for measurement of glucose. The methods described there as well as in the cited documents are herewith included by reference.

Other patents or applications relating to the field and comprising specific information on various modes of applications for enzymes with glucose dehydrogenase activity are U.S. Pat. No. 5,997,817; U.S. Pat. No. 6,057,120; EP 0 620 283; and JP 11-243949-A.

A commercial system which utilizes s-GDH and an indicator that produces a color change when the reaction occurs (Kaufmann, et al., 1997, supra) is the Glucotrend® system distributed by Roche Diagnostics GmbH.

Despite the above discussed advantages for use of a PQQ dependent s-GDH, in the determination of glucose also a disadvantage has to be considered. The enzyme has rather a broad substrate spectrum as compared to m-GDH. That is, s-GDH oxidizes not only glucose but also several other sugars including maltose, galactose, lactose, mannose, xylose and ribose (Dokter et al. 1986 a; Oubrie A., Biochim. Biophys. Acta 1647 (2003) 143-151). The reactivity towards sugars other than glucose may in certain cases impair the accuracy of determining blood glucose levels. In particular patients on peritoneal dialysis, treated with icodextrin (a glucose polymer) may contain in their body fluids, e.g., in blood, high levels of other sugars, especially of maltose (Wens, R., et al., Perit. Dial. Int. 18 (1998) 603-609).

Therefore clinical samples as e.g. obtained from diabetic patients, especially from patients with renal complications and especially from patients under dialysis may contain significant levels of other sugars, especially maltose. Glucose determinations in samples obtained from such critical patients may be impaired by maltose (Frampton, J. E., and Plosker, G. L., Drugs 63 (2003) 2079-2105).

There are few reports in the literature on attempts to produce modified PQQ-dependent s-GDHs with altered substrate specificity. Igarashi, S., et al., Biochem. Biophys. Res. Commun. 264 (1999) 820-824 report that introducing a point mutation at position Glu277 leads to mutants with altered substrate specificity profile.

Sode, EP 1 176 202, reports that certain amino acid substitutions within s-GDH lead to mutant s-GDH with an improved affinity for glucose. In EP 1 167 519 the same author reports on mutant s-GDH with improved stability. Furthermore the same author reports in JP2004173538 on other s-GDH mutants with improved affinity for glucose.

Kratzsch, P. et al., WO 02/34919 report that the specificity of s-GDH for glucose as compared to other sugar substrates, especially as compared to maltose, can be improved by amino acid substitutions in certain positions of s-GDH. Central and crucial is a substitution at amino acid position 348. A mutant s-GDH comprising for example a glycine in position 348 instead of a threonine as present in the wild-type s-GDH has a tremendously improved selectivity for the substrate glucose as, e.g. as compared to the substrate maltose.

However, whereas quite some improvements on glucose specificity have been reported, it appears that such improvements frequently go hand in hand with a reduced stability of s-GDH. For example, it has become evident that the improved specificity of an s-GDH mutant comprising an amino acid substitution in position 348 goes to the expense of stability, especially to the expense of thermo stability. Stability, however, is crucial for example during production and for long term storage, e.g., of glucose test strips.

A great demand and clinical need therefore exists for mutant forms of s-GDH which feature a reasonable thermo stability or both a reasonable thermo stability and an improved specificity for glucose as a substrate.

It was the task of the present invention to provide new mutants or variants of s-GDH with significantly improved thermo stability as compared to the wild-type enzyme or as compared to a mutant with improved specificity but hampered stability.

It has been found that it is possible to significantly improve the thermo stability of wild-type s-GDH as well as of s-GDH mutants designed for improved specificity for glucose, e.g., of an s-GDH mutated at position 348, and to at least partially overcome the above described problems.

The thermo stability has been significantly improved by providing a mutant s-GDH according to the present invention as described in detail herein below and in the appending claims. Due to the improved thermo stability of the new forms of s-GDH, significant technical progress for glucose determinations in various fields of applications is possible.

The improved s-GDH mutants according to this invention can be used with great advantage for the specific detection or measurement of glucose in biological samples, especially by tests strip devices or by biosensors.

SUMMARY OF THE INVENTION

The present invention relates to a mutant protein of PQQ-dependent s-GDH characterized in that in at least one of the positions 122 and 124 the amino acid lysine is present, and wherein these positions correspond to the amino acid positions known from the *A. calcoaceticus* s-GDH wild-type sequence (SEQ ID NO: 2).

Polynucleotide-sequences coding for a mutant protein of s-GDH according to the present invention as well as, an expression vector comprising such polynucleotide sequence, and a host cell comprising said expression vector also represent preferred embodiments of the invention.

The invention further relates to the use of a mutant according to the present invention in a method for measurement of glucose, especially by a tests strip device or with a biosensor.

The following examples, references, sequence listing and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1: Protein sequences of *A. calcoaceticus* PQQ-dependent s-GDH (SEQ ID NO: 2; top) and *A. baumannii* s-GDH (SEQ ID NO: 18; bottom) aligned according to sequence homology.

FIG. 3: Nucleotide (DNA) sequence of the pACSGDH vector referred to in Example 1 containing the wild-type DNA sequence of soluble PQQ-dependent glucose dehydrogenase (SEQ ID NO: 16).

DETAILED DESCRIPTION OF THE INVENTION

Figure 2:
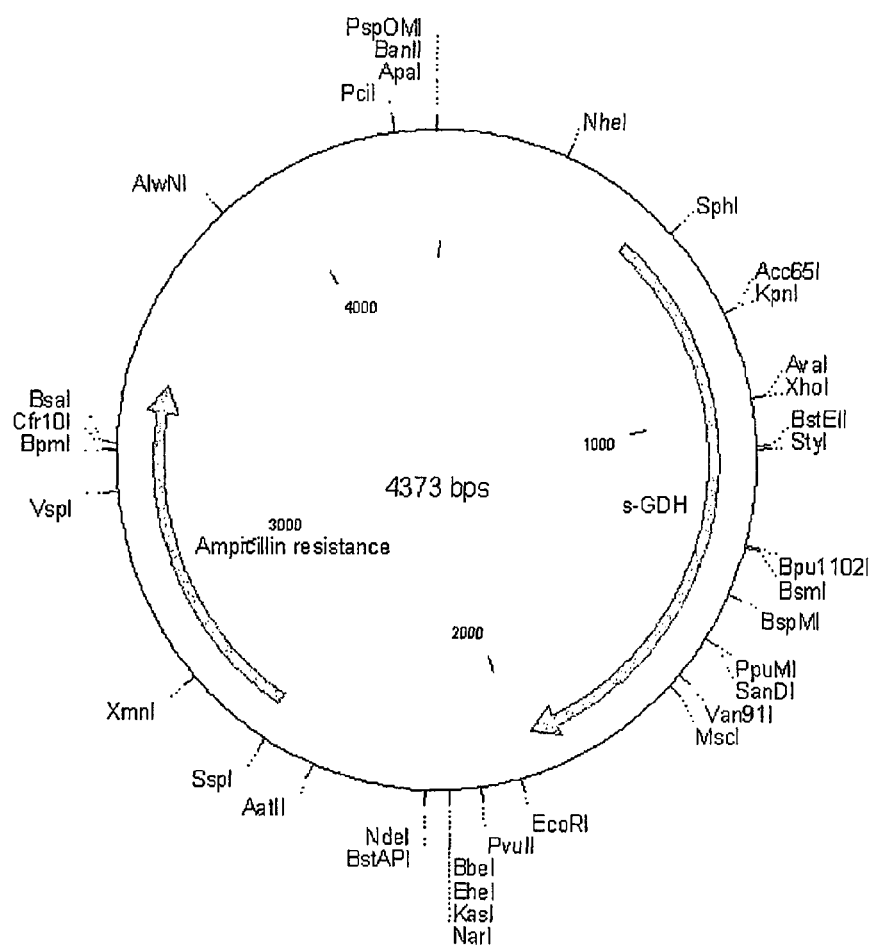
FIG. 2: Illustration of pACSGDH vector referred to in Example 1 containing the wild-type or mutated DNA sequences, respectively, of soluble PQQ-dependent glucose dehydrogenase.

In a first embodiment the invention relates to a mutant protein of PQQ-dependent s-GDH characterized in that in at least one of the positions 122 and 124 the amino acid lysine is present, wherein these positions correspond to the amino acid positions known from the *A. calcoaceticus* s-GDH wild-type sequence (SEQ ID NO: 2).

As discussed above, two completely different quinoprotein enzyme types with glucose dehydrogenase activity (membrane bound and soluble) are grouped together under EC 1.1.5.2. These two types appear not be related to each other.

For the purpose of this invention only the soluble form of GDH (s-GDH) is relevant and improved variants thereof are discussed herein below.

It is known in the art that the wild-type DNA-sequence of a soluble PQQ-dependent glucose dehydrogenase can be isolated from strains of *Acinetobacter*. Most preferred is the isolation from *Acinetobacter calcoaceticus*-type strain LMD 79.41. The polypeptide sequence of this wild-type s-GDH (the mature protein) is given in SEQ ID NO: 2 and the DNA sequence in SEQ ID NO: 1, respectively. Other LMD strains of *Acinetobacter* may also be used as source of wild-type s-GDH. Such sequences can be aligned to the sequence obtained from *A. calcoaceticus* and sequence comparisons be made. It also appears feasible to screen DNA-libraries of other bacterial strains, as for example described for *E. coli* K-12 (Oubrie, A., et al., J. Mol. Biol. 289 (1999) 319-333) and to identify sequences related to s-GDH in such genomes. Such sequences and yet unidentified homologous sequences may be used to generate s-GDH variants with improved thermo stability.

The achievements of the present invention are described in great detail by making reference to amino acid positions known from SEQ ID NO: 2, the wild-type sequence of s-GDH as isolated from *Acinetobacter calcoaceticus*-type strain LMD 79.41. Amino acid positions in different s-GDH isolates corresponding to positions of SEQ ID NO: 2 are easily identified by appropriate sequence comparison.

The multiple alignment and comparison of an s-GDH sequence with the wild-type sequence of SEQ ID NO: 2 preferably is performed with the PileUp program of GCG Package Version 10.2 (Genetics Computer Group, Inc.). PileUp creates a multiple sequence alignment using a simplification of the progressive alignment method of Feng, D. F. and Doolittle, R. F., J. Mol. Evol. 25 (1987) 351-360, and the scoring matrixes for identical, similar, or different amino acid residues are defined accordingly. This process begins with the pair wise alignment of the two most similar sequences, producing a cluster of two aligned sequences. This cluster can then be aligned to the next most related sequence or cluster of aligned sequences. Two clusters of sequences can be aligned by a simple extension of the pair wise alignment of two individual sequences. The final alignment is achieved by a series of progressive, pair wise alignments that include increasingly dissimilar sequences and clusters, until all sequences have been included in the final pair wise alignment. This way amino acid positions in other, homologous s-GDH molecules be easily identified as corresponding to the positions given for *A. calcoaceticus* s-GDH in SEQ ID NO: 2. This is why the amino acid positions given herein shall be understood as amino acid positions of SEQ ID NO: 2 or as the positions corresponding thereto in another, homologous s-GDH molecule.

The term "mutant" or "variant" in the sense of the present invention relates to an s-GDH protein which compared to a corresponding wild-type sequence exhibits at least an amino acid substitution at a position corresponding to position 122 or 124 of SEQ ID NO: 2, wherein the amino acid present in the wild-type is substituted by lysine. The s-GDH mutant may comprise other substitutions and/or deletions and/or insertions provided that an s-GDH mutant of the invention does not differ by more than 50 amino acids from the s-GDH of SEQ ID NO: 2, e.g. that it exhibits at most 50 amino acid substitutions in total.

As mentioned above, improvements in glucose specificity appear to be possible largely at the expense of a reduced stability. As the skilled artisan will appreciate stability may relate to different aspects, like storage temperature and/or storage time, respectively. Short term temperature stress models are frequently used to assess stability. Stability according to the present invention is assessed in such a short term stress model and thus referred to as thermo stability. Thermo stability is determined by measuring the unstressed and stressed s-GDH enzyme activity of a sample. By setting the unstressed sample activity to 100% the remaining activity after stress treatment can be calculated in percent. For mutants of s-GDH with improved substrate specificity, 65° C. for 30 minutes were chosen Using these conditions the wild-type enzyme has about 80% of its original activity left, whereas most of the mutants with improved specificity for glucose have only 10% or less of their initial enzymatic activity left after performing this short-term stress model.

It has been found that two positions of s-GDH appear to be rather critical for achieving significant improvements in terms of thermo stability, i.e., positions 122 and 124. It has also been found that only the substitution by one of the 20 naturally occurring amino acids, the amino acid lysine, has a striking effect on thermo stability. The substitution by lysine at position 122 and/or 124 improves thermo stability of the wild-type s-GDH enzyme. The wild-type enzyme is rather stable at any rate but thermo stability is further improved by a lysine in position 122 and/or 124. What is of significant relevance is the fact that it has been found that these substitutions also have a pronounced effect on the thermo stability of mutants which previously had been generated in order to improve glucose specificity, but at the expense of a reduced thermo stability.

In a preferred embodiment the s-GDH mutant according to the present invention comprises a lysine in position 122 with said position corresponding to position 122 known from *A. calcoaceticus* wild-type s-GDH (SEQ ID NO: 2).

In another preferred embodiment the s-GDH mutant according to the present invention comprises a lysine in position 124 with said position corresponding to position 124 known from *A. calcoaceticus* wild-type s-GDH (SEQ ID NO: 2).

In still another preferred embodiment the s-GDH mutant according to the present invention comprises a lysine in position 122 and 124 with said positions corresponding to positions 122 and 124, respectively, known from *A. calcoaceticus* wild-type s-GDH (SEQ ID NO: 2).

As mentioned above, it is crucial that the thermo stability of s-GDH mutants with improved specificity for glucose, e.g., of the mutants disclosed in WO 02/34919 can be improved. It has been found and is demonstrated that this can be accomplished by the substitution of the naturally occurring amino acids by a lysine in position 122 and/or 124. In a very preferred embodiment the present invention therefore relates to an s-GDH mutant comprising a lysine in position 122 and/or 124 and additionally comprising one or more other modifications leading to an improved specificity for glucose, especially as compared to maltose.

A preferred mutant according to the present invention is characterized in that relative to the s-GDH wild-type enzyme as isolated from *A. calcoaceticus*, it has an at least two-fold improved substrate specificity for glucose as compared to at least one other selected sugar substrate and at the same time a thermo stability that is at least 20% of the thermo stability as measured for the wild-type enzyme.

In order to calculate the substrate specificity or cross-reactivity one easy way is to set the activity measured with glucose as substrate to 100% and to compare the activity measured with the other selected sugar to the glucose value. Sometimes, in order not to be redundant, simply the term specificity is used without making special reference to glucose on the one hand and a selected other sugar substrate on the other hand.

The expert in the field will appreciate that comparison of enzymatic activities is best made at equimolar concentrations of the substrate molecules investigated using well-defined assay conditions. Otherwise corrections for differences in concentrations have to be made.

Standardized and well-defined assay conditions have to be chosen in order to assess (improvements in) substrate specificity. The enzymatic activity of s-GDH for glucose as a substrate as well as for other selected sugar substrates is measured as described in the Examples section.

Based on these measurements of enzymatic activity for glucose or a selected different sugar, preferably maltose, cross-reactivity (and improvements thereof) is assessed.

The s-GDH (cross-) reactivity for a selected sugar in percent is calculated as

Cross-reactivity [%]=(activity selected sugar/activity glucose)×100%.

(Cross-) reactivity for maltose of wild-type s-GDH according to the above formula has been determined as about 105% (see Example 7).

(Improved) specificity is calculated according to the following formula:

$$\text{specificity(improvement)} = \frac{\text{activity glucose mutant}}{\text{activity selected sugar mutant}} \times \frac{\text{activity selected sugar wild-type}}{\text{activity glucose wild-type}}$$

As compared to the wild-type enzyme, an s-GDH form with an at least 10-fold improvement in specificity for glucose versus maltose (maltose/glucose) accordingly with maltose as substrate has at most 10.5% of the activity as measured with glucose as substrate. Or, if, for example a mutant s-GDH has cross-reactivity for maltose of 20% (determined and calculated as described above), this mutant as compared to the wild-type s-GDH therefore has a 5.25 fold improved substrate specificity (maltose/glucose).

The term "specific activity" for a substrate is well known in the art, it is preferably used to describe the enzymatic activity per amount of protein. Various methods are known to the art to determine specific activity of GDH molecules, using glucose or other sugars as substrates (Igarashi, S., et al., (1999) supra). A preferred method available for such measurement is described in detail in Example 8.

Whereas it is possible, to select many different sugar molecules and to investigate the glucose specificity of s-GDH in comparison to any such selected sugar molecule, it is preferred to select a clinically relevant sugar molecule for such a comparison. Preferred selected sugars are selected from the group consisting of mannose, allose, galactose, xylose, and maltose. Preferably, maltose or galactose is selected and mutant s-GDH is tested for improved substrate specificity for glucose as compared to galactose or maltose. In a further preferred embodiment the selected sugar is maltose.

In a preferred embodiment a mutant protein of PQQ-dependent s-GDH according to the present invention comprises a lysine at position 122 and/or 124 and additionally one or more amino acid substitution(s) at one or more position(s) selected from the group consisting of positions 16, 22, 65, 76, 116, 120, 127, 143, 168, 169, 171, 177, 224, 227, 230, 231, 245, 246, 255, 277, 287, 294, 295, 299, 302, 305, 307, 308, 317, 321, 323, 341, 348, 349, 354, 355, 364, 378, 422, 425, 428 and 438. Most of the above positions have been previously shown to influence the specificity of s-GDH for glucose as compared to other selected sugars, especially as compared to the substrates maltose. The full disclosure of WO 02/34919 is herewith included by reference.

As described in WO 02/34919, a substitution of the amino acid in position 348 of the s-GDH sequence corresponding to the wild-type sequence isolated from *A. calcoaceticus*, can be used to significantly improve the glucose specificity of s-GDH. In an especially preferred embodiment the present invention relates to an s-GDH mutant comprising a lysine in position 122 and/or 124 and an amino acid substitution at position 348. Preferably the residue threonine at position 348 is substituted with an amino acid residue selected from the group consisting of alanine, glycine, and serine. In a more preferred embodiment glycine is used to substitute for threonine at position 348. The terminology T348G is known to the skilled artisan and indicates that threonine at position 348 is replaced by glycine.

In a further preferred embodiment the variant s-GDH comprising a lysine in position 122 and/or 124 is characterized in that the amino acid residue asparagine at position 428 is substituted with an amino acid residue selected from the group consisting of leucine, proline and valine. More preferred the substitution in position 428 is by proline.

One group of preferred s-GDH variants according to this invention comprising a lysine in position 122 and/or 124 is further characterized in that the amino acid residue threonine at position 348 and the amino acid asparagine at position 428 are both substituted, wherein preferred substitutions are the ones outlined above.

The mutants according to the present invention comprising a lysine in position 122 and/or 124 may optionally further be modified to comprise one or more amino acid substitutions at amino acid positions corresponding to positions 169, 171, 245, 341, and/or 349 of the s-GDH wild-type sequence known from *A. calcoaceticus* (SEQ ID NO: 2).

In case the amino acid corresponding to position 169 of the s-GDH wild-type sequence known from *A. calcoaceticus* (SEQ ID NO: 2) is substituted in a variant of the present invention, it is preferred that the naturally occurring amino acid leucine is substituted by phenylalanine, tyrosine or tryptophane. More preferred the substitution in position 169 is by phenylalanine.

In case the amino acid corresponding to position 171 of the s-GDH wild-type sequence known from *A. calcoaceticus* (SEQ ID NO: 2) is substituted in a variant of the present invention, it is preferred that the naturally occurring amino acid tyrosine is substituted by an amino acid selected from the group consisting of from the group consisting of alanine, methionine, glycine. More preferred the substitution in position 171 is by glycine.

In case the amino acid corresponding to position 245 of the s-GDH wild-type sequence known from *A. calcoaceticus* (SEQ ID NO: 2) is substituted in a variant of the present invention, it is preferred that the naturally occurring amino acid glutamic acid is substituted by aspartic acid, asparagine or glutamine. More preferred the substitution in position 245 is by aspartic acid.

In case the amino acid corresponding to position 341 of the s-GDH wild-type sequence known from *A. calcoaceticus* (SEQ ID NO: 2) is substituted in a variant of the present invention, it is preferred that the naturally occurring amino acid methionine is substituted by valine, alanine, leucine or isoleucine. More preferred the substitution in position 341 is by valine.

In case the amino acid corresponding to position 349 of the s-GDH wild-type sequence known from *A. calcoaceticus* (SEQ ID NO: 2) is substituted in a variant of the present invention, it is preferred that the naturally occurring amino acid valine is substituted by alanine or glycine. More preferred the substitution in position 349 is by alanine.

It has been also found that it is possible to further improve substrate specificity of an s-GDH variant by insertion of an amino acid between position 428 and 429. Such mutants comprising an amino acid insertion between amino acid 428 and amino acid 429 also represent a preferred starting material for generating mutants exhibiting both improved stability as well as improved specificity. In a preferred embodiment the present invention relates to a mutant s-GDH comprising a lysine in position 122 and/or 124 as well as an amino acid insertion between position 428 and position 429 of s-GDH.

In a further preferred embodiment the s-GDH mutant according to the present invention in addition to having a lysine in position 122 and/or 124 carries an insertion between amino acid residues 428 and 429 and comprises at least two amino acid substitutions selected from the group consisting of positions 171, 245, 341, 348 and 349 as corresponding to amino acid positions of the s-GDH wild-type sequence known from *A. calcoaceticus* (SEQ ID NO: 2).

In yet a further preferred embodiment the s-GDH mutant according to the present invention in addition to having a lysine in position 122 and/or 124 carries an insertion between amino acid residues 428 and 429 and comprises at least three amino acid substitutions selected from the group consisting of positions 171, 245, 341, 348 and 349 as corresponding to amino acid positions of the s-GDH wild-type sequence known from *A. calcoaceticus* (SEQ ID NO: 2).

As the skilled artisan will appreciate, it is possible to undertake amino acid substitutions, e.g. silent mutations, which do not influence the properties of s-GDH to a significant extend. The variant according to the present invention will, however, have no more than 50 amino acid exchanges as compared to SEQ ID NO: 2. Preferably, the variant will comprise 20 or less amino acid substitutions, more preferred, only 10 amino acid substitutions or fewer substitutions will be present.

Some specific s-GDH variants according to the present invention are given in the Examples section. S-GDH variants with low glucose interference and acceptable thermo stability comprise mutants with substitutions in the following positions 65+122+124+171+245+341+348+426+428+430+436, 65+122+124+171+245+341+348+426+428+430 and 122+124+171+245+246+341+348+425+428, respectively. These three variants represent farther preferred embodiments of the present invention.

Amino acid sequence analysis revealed that the sequence motives found in wild-type s-GDH from *A. calcoaceticus* on the one hand and *A. baumannii* on the other hand appear to be very conservative around the positions 122 and 124 that are of major relevance to improve thermo stability as identified and shown in the present invention.

A variant of PQQ-dependent s-GDH, comprising the amino acid sequence of TYNKSTD (SEQ ID NO: 3), wherein either the asparagine (N) or the serine (S) is replaced by a lysine represents a preferred embodiment of the present invention. SEQ ID NO: 17 corresponds to position 120-126 of *A. calcoaceticus* wild-type s-GDH or to position 120-126 of *A. baumannii* wild-type s-GDH but comprises either a lysine in position 122 (=Xaa$_1$) or in position 124 (=Xaa$_2$) or in both these positions, thus replacing the naturally occurring amino acids asparagine or/and serine, respectively (*A. calcoaceticus*).

Numerous possibilities are known in the art to produce mutant proteins. Based on the important findings of the present invention disclosing the critical importance of a lysine in position 122 and/or 124 of a mutant s-GDH the skilled artisan now can easily produce further appropriate variants of s-GDH harboring these and other favorable modifications. Such variants for example can be obtained by the methods known as random mutagenesis (Leung, D. W., et al., Technique 1 (1989) 11-15) and/or site directed mutagenesis (Hill, D. E., et al., Methods Enzymol. 155 (1987) 558-568). An alternative method to produce a protein with the desired properties is to provide chimaeric constructs, which contain sequence elements from at least two different sources or to completely synthesize an appropriate s-GDH gene. Such procedures known in the art may be used in combination with the information disclosed in the present invention to provide mutants or variants of s-GDH comprising e.g. additional amino acid substitutions in combination with the disclosed critical importance of a lysine in position 122 and/or 124, e.g., of SEQ ID NO: 2.

An s-GDH variant according to the present invention can e.g., be produced by starting from an s-GDH gene as isolated from *Acinetobacter calcoaceticus*-type strain LMD 79.41 as well as by starting from a homologous sequence. In the context of this application the term "homologous" is meant to comprise an s-GDH amino acid sequence with at least 90% identity as compared to SEQ ID NO: 2. With other words, after appropriate alignment using the PileUp program, at least 90% of the amino acids of such homologous s-GDH are identical to the amino acids described in SEQ ID NO: 2.

It will be understood that variations of DNA and amino acid sequences naturally exist, or may be intentionally introduced using methods known in the art. These variations may result in up to 10% amino acid differences in the overall sequence, due to deletions, substitutions, insertions, inversions or additions of one or more amino acid residues in said sequence as compared to SEQ ID NO: 2. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, and tyrosine. Other contemplated variations include salts and esters of the afore mentioned polypeptides, as well as precursors of the aforementioned polypeptides, for example, precursors having an N-terminal substitution such as methionine, N-formylmethionine used as leader sequences. Such variations may be made without necessarily departing from the scope and the spirit of the present invention.

According to procedures known in the state of the art or according to the procedures given in the examples section, it is possible to obtain polynucleotide sequences coding for any of the s-GDH mutants as discussed above. The invention therefore comprises also isolated polynucleotide sequences encoding s-GDH mutant proteins according to the present invention as described above.

The present invention further includes an expression vector comprising a nucleic acid sequence according to the present invention operably linked a promoter sequence capable of directing its expression in a host cell.

The present invention further includes an expression vector comprising a nucleic acid sequence according to the present invention operably linked to a promoter sequence capable of directing its expression in a host cell. Preferred vectors are plasmids such as pACSGDH shown in FIGS. 2 and 3.

Expression vectors useful in the present invention typically contain an origin of replication, an antibiotic resistance for selection, a promoter for expression and the whole or part of the s-GDH gene variant. The expression vectors may also include other DNA sequences known in the art, like signal sequences (for a better folding, transportation into the periplasma or secretion), inducers for a better modulation of the expression, or cleavage sites for cloning.

The characteristics of the selected expression vector must be compatible to the host cell, which is to be employed. For example, when cloning in an *E. coli* cell system, the expression vector should contain promoters isolated from the genome of *E. coli* cells (e.g., lac, or trp). Suitable origins of replication like the ColE1 plasmid replication origin can be used. Suitable promoters include, for example, lac and trp.

It is also preferred that the expression vector includes a sequence coding for a selection marker like an antibiotic resistance gene. As selectable markers, ampicillin resistance, or canamycin resistance may be conveniently employed. All of these materials are known in the art and are commercially available.

Suitable expression vectors containing the desired coding and control sequences may be constructed using standard recombinant DNA techniques known in the art, many of which are described in Sambrook et al., in "Molecular Cloning: A Laboratory Manual" (1989) Cold Spring Harbor, N.Y., Cold Spring Harbour Laboratory Press.

The present invention additionally relates to host cells containing an expression vector which comprises a DNA sequence coding for all or part of the mutant s-GDH. The host cells preferably contain an expression vector that comprises all or part of one of the DNA sequences coding for a mutant s-GDH having one or more mutations shown in the Examples 2-8. Suitable host cells include, for example, *E. coli* HB101 (ATCC 33694) available from Promega (2800 Woods Hollow Road, Madison, Wis., USA), XL1-Blue MRF' available from Stratagene (11011 North Torrey Pine Road, La Jolla, Calif., USA) and the like.

Expression vectors may be introduced into host cells by various methods known in the art. For example, transformation of host cells with expression vectors can be carried out by polyethylene glycol mediated protoplast transformation method (Sambrook et al. 1989, supra). However, other methods for introducing expression vectors into host cells, for example, electroporation, bolistic injection, or protoplast fusion, can also be employed.

Once an expression vector containing an s-GDH variant has been introduced into an appropriate host cell, the host cell may be cultured under conditions permitting expression of the desired s-GDH variants. Host cells containing the desired expression vector with the DNA sequence coding for all or part of the mutant s-GDH can be easily identified by i.e. antibiotica selection. The expression of the s-GDH variants can be identified by different methods like measuring production of s-GDH mRNA transcripts, detection of the gene product immunologically or detection of the enzymatic activity of the gene product. Preferably an enzymatic assay is applied.

The present invention also teaches the generation and screening of s-GDH mutants. Random mutagenesis and saturation mutagenesis is performed as known in the art. Variants are screened for thermo stability (activity without heat stress treatment compared to remaining activity after heat stress treatment). The assay conditions chosen are adapted to ensure that the expected small enhancements brought about e.g., by a single amino acid substitution, can be measured. One preferred mode of selection or screening of appropriate mutants is given in Example 3. Any change or improvement as compared to the starting enzyme (mutant or wild-type) can be clearly detected.

It should, of course, be understood that not all expression vectors and DNA regulatory sequences would function equally well to express the DNA sequences of the present invention. Neither will all host cells function equally well with the same expression system. However, one of ordinary skill in the art will make an appropriate selection among the expression vectors, DNA regulatory sequences, and host cells using the guidance provided herein without undue experimentation.

The invention also relates to a process for producing s-GDH variants of the current invention comprising culturing a host cell of the invention under conditions suitable for production of the mutant s-GDH of the invention. For bacterial host cells, typical culture conditions are liquid medium containing carbon and nitrogen sources, the appropriate antibiotic and induction agent (depending on the used expression vector). Typical appropriate antibiotics include ampicillin, canamycin, chloroamphenicol, tetracycline and the like. Typical induction agents include IPTG, glucose, lactose and the like.

It is preferred that the polypeptides of the present invention are obtained by production in host cells expressing a DNA sequence coding the mutant s-GDH. The polypeptides of the present invention may also be obtained by in vitro translation of the mRNA encoded by a DNA sequence coding for the mutant s-GDH. For example, the DNA sequences may be synthesized as described above and inserted into a suitable expression vector, which in turn may be used in an in vitro transcription/translation system.

An expression vector comprising an isolated polynucleotide as defined and described above operably linked to a promoter sequence capable of promoting its expression in a cell-free peptide synthesis system represents another preferred embodiment of the present invention.

The polypeptides produced e.g. by procedures as describe above, may then be isolated and purified using various routine protein purification techniques. For example, chromatographic procedures such as ion exchange chromatography, gel filtration chromatography and affinity chromatography may be employed.

One of the major applications of the improved s-GDH variants of this invention is for the use in test strips to monitor the blood-glucose level in diabetic patients. The insensitivity of PQQ-dependent glucose dehydrogenase towards oxygen is, as discussed above, a big advantage over glucose oxidase. The interference due to e.g., maltose, galactose, and/or other related sugars which may be present in a sample to be analyzed, can now be significantly reduced using the novel s-GDH variants having both improved thermo stability as well as improved specificity towards glucose. Of course many kinds of samples may be investigated. Bodily fluids like serum, plasma, intestinal fluid or urine are preferred sources for such samples.

The invention also comprises a method of detecting, determining or measuring glucose in a sample using an s-GDH mutant according to the present invention. It is especially preferred that the improved method for detection of glucose in a sample is characterized in that said detection, determination or measurement of glucose is performed using a sensor or test strip device.

Also within the scope of the present invention is a device for the detection or measurement of glucose in a sample comprising an s-GDH mutant according to this invention as well as other reagents required for said measurement.

The s-GDH variants with improved thermo stability of this invention can also be used to great advantage in biosensors (D'Costa, E. J., et al., Biosensors 2 (1986) 71-87; Laurinavicius, V., et al., Analytical Letters 32 (1999) 299-316; Laurinavicius, V., et al., Monatshefte fuer Chemie 130 (1999) 1269-1281; Malinauskas, A. et al., Sensors and Actuators, B: Chemical 100 (2004) 395-402) for online monitoring of glucose in a sample or a reactor. For this purpose, the s-GDH variants can, for example, be used to coat an oxygen-insensitive glassy electrode with an osmium complex containing a redox conductive epoxy network (Ye et al., 1993 supra) for more accurate determination of the glucose concentration.

In the following examples, all reagents, restriction enzymes, and other materials were obtained from Roche Diagnostics Germany, unless other commercial sources are specified, and used according to the instructions given by the suppliers. Operations and methods employed for the purification, characterization and cloning of DNA are well known in the art (Ausubel, F., et al., in "Current protocols in molecular biology" (1994), Wiley) and can be adapted as required by the skilled artisan.

The following examples further illustrate the present invention. These examples are not intended to limit the scope of the present invention, but provide further understanding of the invention.

Example 1

Cloning and Expression of the Wild-Type *A. calcoaceticus* Soluble PQQ-Dependent Glucose Dehydrogenase in *E. coli*

The s-GDH gene was isolated from *Acinetobacter calcoaceticus* strain LMD 79.41 according to standard procedures. The wild-type s-GDH gene was subcloned into a plasmid containing the mgl promoter for adjustable expression (cf. Patent application WO 88/09373). The new construct was called pACSGDH (see FIGS. 2 and 3). The recombinant plasmids were introduced into a host organism selected from the *E. coli* group. These organisms were then cultivated under appropriate conditions and colonies showing s-GDH activity selected.

The plasmid pACSGDH was isolated from a 200 ml overnight culture of the clone mentioned above using the QIAGEN Plasmid Maxi Kit (Qiagen) according to the manufacturers' protocol. The plasmid was resuspended in 1 ml bi-distilled water. The concentration of the plasmid was determined using a Beckman DU 7400 Photometer.

The yield was 600 µg. Then the quality of the plasmid was determined by agarose gel electrophoresis.

Example 2

Mutagenic PCR

To generate random mutations in the s-GDH-gene, mutagenic PCR (polymerase chain reaction) was performed. The pACSGDH plasmid and the DNA sequence encoding the mutated enzymes (PCR product from mutagenic PCR) were digested with the restriction enzymes Sph I and Eco RI. The products were gel purified. The digested DNA sequences were ligated and an aliquot of the ligation reaction mixture was used to transform competent *E. coli* cells. The transformants were subsequently selected on LB-plates containing ampicillin.

Individual colonies were chosen, grown over night in LB-medium containing ampicillin and subjected to screening (see Example 3).

Mutagenic PCR Reaction Mixture:
40 ng pACSGDH
1× buffer without MgCl2 (Roche Diagnostics GmbH, Cat. 1699 105)
dCTP, dTTP 1 mM
dATP, dGTP 0.2 mM (Roche Diagnostics GmbH, Cat. 1969 064)

```
                                              (= SEQ ID NO: 4)
40 pmol      (5'-CGC GCA CGC GCA TGC CGC CGA
GF23-Primer   TGT TC)

(= SEQ ID NO: 5)
40 pmol GR23 (5'-GAC GGC CAG TGA ATT CTT TTC
              TA)
```

7 mM MgCl2
0.6 mM MnCl2
5 U Taq DNA polymerase (Roche Diagnostics GmbH, Cat. 1146 165)
Gene Amp PCR System 2400 (Perkin Elmer), 30 cycles: 95° C., 1 min, 45° C. 2 min, 72° C. 2 min Purification of the PCR products using the High Pure PCR Product Purification Kit from Roche Diagnostics GmbH (Cat. 1 732 676) according to the manufacturer's protocol.

Digestion of the PCR-fragments with 25 U SphI (Roche Diagnostics GmbH, Cat. 606 120) in 1× buffer H (Roche Diagnostics GmbH, Cat. 1 417 991) at 37° C. over night; addition of 25 U EcoRI (Roche Diagnostics GmbH, Cat. 703 737) and further digestion for 3.5 hours.

Digestion of 50 µg pACSGDH with 180 U SphI and 180 U EcoRI in 1× buffer H for 4 hours at 37° C.

Gel electrophoresis of the digested pACSGDH and the digested fragments using agarose gels (0.8%).

Extraction of the DNA molecules using QIAquick Gel Extraction Kit (Qiagen, Cat. 28706) according to the manufacturer's protocol.

Determination of the concentration of the fragments and the digested vector using a Beckman DU 7400 Photometer.

Determination of the quality of the purified products by agarose gel electrophoresis.

Ligation of 100 ng digested vector with 140 ng mPCR-fragments using 1 U T4-DNA-Ligase (Roche Diagnostics GmbH, Cat. 481 220) in a volume of 20 µl at 16° C. over night.

Electroporation of electrocompetent XL1F-cells (Stratagene) with 1 µl of the ligation reaction with 2.5 KV in 0.2 cm cuvettes using a BioRad *E. coli* Pulser (BioRad).

After growth in 1 ml LB at 37° C. for one hour, bacteria were plated on LB-Ampicillin agar plates (100 µg/ml Ampicillin) and grown over night at 37° C.

50% of the expressed clones produced enzymatically active s-GDH that was subjected to the following screening method.

Example 3

Screening for Thermo Stability

The mutant colonies on the agar plates described above where picked into microtiter plates (MTPs) containing 200 µl LB-Ampicillin-media/well and incubated over night at 37° C. These plates are called master plates.

From each master plate, 5 µl sample/well was transferred to an MTP containing 5 µl per/well of B (B=Bacterial Protein Extraction Reagent; Pierce No. 78248) for cell disruption and 240 µl of 0.0556 mM pyrroloquinoline quinone (PQQ); 50 mM Hepes; 15 mM CaCl$_2$ pH 7.0/well for activation of s-GDH were added. To complete the formation of the holoenzyme, the MTP was incubated at 25° C. for 2 hours and at 10° C. over night. This plate is called working plate.

From the working plate 2×10 µl sample/cavity were transferred to two empty MTPs. One MTP was subjected to a short time temperature stress (30 minutes at 70° C./incubator). After cooling to room temperature the stressed and untreated MTP were tested with 90 µl of mediator solution containing 30 mM glucose (see Example 8).

The dE/min was calculated and the values from the unstressed samples were set to 100% activity. The values obtained with the temperature stressed MTP were compared to the untreated values and calculated in percent activity ((e.g.: dE/min tempered/dE untreated)*100). This is equivalent to the thermo stability of the (variant) enzyme expressed in percent remaining activity. In order to compensate the deviations of results due to fluctuation of the distribution of heat in the MTPs during incubation, wild-type enzyme was added as reference to each plate in dedicated cavities.

The following mutant has been identified:

| Enzyme | % remaining activity after 30 minutes 70° C. | Amino acid exchanges |
| --- | --- | --- |
| WT | 3-20% | — |
| Mutant A | 9-30% | N122K, L202I |

The variability of remaining activity is due to uneven heat distribution in the wells of the MTP and decay of holoenzyme during heating to apoenzyme and coenzyme and spontaneous reassembly to holoenzyme after thermal stress. Nevertheless the mutant A consistently showed a higher value for remaining enzymatic activity than the wild-type enzyme.

Example 4

Sequencing of the Gene Coding for s-GDH Mutant A

The plasmid containing the gene for s-GDH mutant A, which has a higher thermo stability than the wild-type was isolated (High Pure Plasmid Isolation Kit, Roche Diagnostics GmbH, No. 1754785) and sequenced using an ABI Prism Dye Terminator Sequencing Kit and ABI 3/73 and 3/77 sequencer (Amersham Pharmacia Biotech).

The following primers were used:

Sense Strand:

```
                                         (= SEQ ID NO: 6)
GDH 1:  5'-TTA ACG TGC TGA ACA GCC GG-3'

(= SEQ ID NO: 7)
GDH 2:  5'-ATA TGG GTA AAG TAC TAC GC -3'
```

Result:
The amino acid exchanges of mutant A already listed in the table of Example 3 were found.

Example 5 s-GDH Mutants Obtained by Saturation Mutagenesis

Saturation mutagenesis was performed to see if both or only single amino acid exchanges in mutant A are responsible for the thermal stability improvement. Furthermore the method allows one to see if the found effect could be enhanced by other amino acid exchanges at the positions identified. The QuikChange Site-Directed Mutagenesis Kit (Stratagene, Cat. 200518) was used to substitute successively wild type amino acids at positions 122 and 202 of the wild-type s-GDH-protein, respectively.

The 5'- and the 3'-primer used for mutagenesis were complementary to each other and contained NNN in a central position. These 3 random synthesized nucleotides, which are at the desired position (122 or 202, respectively), were flanked by 12 to 16 nucleotides at each end which were identical to the sense and antisense DNA-strand of the template. Instead of the codon, the primer contained NNN therefore the oligonucleotides code for every possible codon.

For each of the positions 122 and 202, respectively, one PCR reaction was performed.

The PCR-reactions and the DpnI-restriction endonuclease digestions were performed according to the manual.

After that, 1 μl of each reaction was used for the electroporation of XL1F-cells. Cells were grown and the s-GDH-activities of the clones were determined as described above.

To increase the statistical likelihood that all 20 possible amino acids substitutions are covered in this evaluation, 200 clones were screened (see Example 3) for each position.

The following primers where used:

```
for position 122
                                       (SEQ ID NO: 8)
Sense stand  5'- TCGTTATACCTATNNNAAATCAACAGATA-3'

(SEQ ID:NO: 9)
Antisense    5'- TATCTGTTGATTTNNNATAGGTATAACGA-3'
strand for position
202
                                       (SEQ ID NO: 10)
Sense strand 5'-TAAAGTACTACGCNNNAATCTTGATGGAA-3'

(SEQ ID NO: 11)
Antisense    5'-TTCCATCAAGATTNNNGCGTAGTACTTTA-3'
strand
```

Results:

The amino acid exchange at position 202 didn't change the thermo stability. Only the wobble at position 122 produced clones with enhanced thermal stability. The best exchange was N122K.

Example 6

Generating Mutants with High Substrate Specificity for Glucose as Compared to Maltose and Enhanced Thermo Stability

In WO 02/34919 several amino acid exchanges at different positions of s-GDH have been identified and shown to enhance the substrate specificity for glucose as compared to e.g., maltose. Combinations of the amino acid exchange T348G with amino acid substitutions at other positions for example at positions 169, 171, 245, 341 and/or 349 enhanced the substrate specificity furthermore. Several of these described mutants were selected to improve their thermo stability by introducing the found amino acid exchange N122K. The point mutation was accomplished by using the following primers.

```
                                       (SEQ ID NO: 12)
Sense stand 5'-TCGTTATACCTATAAGAAATCAACAGATA -3'

(SEQ ID:NO: 13)
Antisense   5'- TATCTGTTGATTTCTTATAGGTATAACGA-3'
strand
```

The same screening for thermo stability, as in Example 3 described, was applied, only the incubation temperature was reduced from 70° C. to 65° C. for 30 minutes.

Results:

| Enzyme | Maltose/Glucose (30 mM sugar in %) | % remaining activity after 30 minutes at 65° C. | Amino acid exchanges |
|---|---|---|---|
| WT | 105% | 80% | — |
| Template B/0 | 4% | 5% | Y171G + E245D + M341V + T348G + in429P |
| Mutant B/1 | 4% | 10% | N122K + Y171G + E245D + M341V + T348G + in429P |
| Template C/0 | 2% | 10% | Y171G + E245D + M341V + T348G + A426S + N428P + Q430M |
| Mutant C/1 | 2% | 20% | N122K + Y171G + E245D + M341V + T348G + A426S + N428P + Q430M |
| Template D/0 | 4% | 20% | Y171G + E245D + Q246H + M341V + T348G + T425V + N428P |
| Mutant D/1 | 4% | 30% | Y171G + N122K + E245D + Q246H + M341V + T348G + T425V + N428P |

It can be clearly seen that on all mutant types the additional amino acid exchange N122K produced an enhancement of thermo stability in the chosen stress model without affecting the substrate specificity.

Example 7

Generating Mutants with High Substrate Specificity and Further Enhanced Thermo Stability

While screening for enhanced substrate specificity as e. g. described in WO 02/34919, using m-PCR and saturation mutagenesis at random positions the spectrum of screening parameters was expanded for thermo stability as above described.

Starting with a mutant E/0 with high substrate specificity for glucose compared to maltose (2%) with the amino acid exchanges Y171G+E245D+M341V+T348G+N428P a new amino acid exchange S124K was found.

This new exchange was then applied to the already improved mutants containing N122K of Example 6 using the following primers:

```
                                       (SEQ ID NO: 14)
Sense strand 5'- CCTATAAGAAAAGACAGATACGCTCG -3'

(SEQ ID:NO: 15)
Antisense    5'- CGAGCGTATCTGTCTTTTTCTTATAGG-3'
strand
```

Results:

| Enzyme | Maltose/Glucose (30 mM sugar in %) | % remaining activity after 30 minutes at 65° C. | Amino acid exchanges |
|---|---|---|---|
| WT | 105% | 80% | — |
| Mutant B/1 | 4% | 10% | N122K + Y171G + E245D + M341V + T348G + in429P |
| Mutant B/2 | 4% | 15% | N122K + S124K + Y171G + E245D + M341V + T348G + in429P |

-continued

| Enzyme | Maltose/ Glucose (30 mM sugar in %) | % remaining activity after 30 minutes at 65° C. | Amino acid exchanges |
| --- | --- | --- | --- |
| Mutant C/1 | 2% | 20% | N122K + Y171G + E245D + M341V + T348G + A426S + N428P + Q430M |
| Mutant C/2 | 2% | 25% | N122K + S124K + Y171G + E245D + M341V + T348G + A426S + N428P + Q430M |
| Mutant D/1 | 4% | 30% | N122K + Y171G + E245D + Q246H + M341V + T348G + T425V + N428P |
| Mutant D/2 | 4% | 40% | N122K + 124K + Y171G + E245D + Q246H + M341V + T348G + T425V + N428P |
| Mutant E/0 | 2% | 10% | Y171G + E245D + M341V + T348G + N428P |
| Mutant E/1 | 2% | 20% | Y171G + S124K + E245D + M341V + T348G + N428P |

The above results show that the amino acid exchanges on positions N122K and S124K have an additive, positive effect on the thermo stability of the mutants.

Example 8

Purification of Wild-type or Variant s-GDH and Analysis of Enzymatic Activity Respectively E. coli cells were grown (LB-Amp. 37° C.), harvested and resuspended in potassium phosphate buffer pH 7.0. Cell disruption was performed by French Press passage (700-900 bar). After centrifugation the supernatant was applied to an S-Sepharose (Amersham Pharmacia Biotec) column equilibrated with 10 mM potassium phosphate buffer pH 7.0. After washing, the s-GDH was eluted using a salt gradient 0-1 M NaCl. The fractions showing s-GDH activity were pooled, dialyzed against potassium phosphate buffer pH 7.0 and re-chromatographed on re-equilibrated S-Sepharose column. The active fractions were pooled and subjected to a gel filtration using a Superdex® 200 column (Amersham). The active fractions were pooled and after addition of $CaCl_2$ (3 mM end concentration) stored at −20° C.

Enzyme Assay and Protein Determination of Purified Wild-Type and Variant s-GDH, Respectively Protein determination was performed using the Protein Assay Reagent no. 23225 from Pierce (calibration curve with BSA, 30 Min. 37° C.).

The s-GDH samples were diluted to 1 mg protein/ml with 0.0556 mM pyrollo-quinoline quinone(PQQ); 50 mM Hepes; 15 mM $CaCl_2$ pH 7.0 and incubated at 25° C. for 30 minutes for reconstitution or activation.

After activation, samples were diluted with 50 mM Hepes; 15 mM $CaCl_2$ pH 7.0 to approximately 0.02 U/ml, and 50 μl of each diluted sample was added to 1000 μl of a 0.2 M citrate buffer solution (pH 5.8; at 25° C.) containing 0.315 mg (4-(dimethylphosphinylmethyl)-2-methyl-pyrazolo-[1.5a]-imidazol-3-yl)-(4-nitro-sophenyl)-amine (see U.S. Pat. No. 5,484,708)/ml as a mediator and 30 mM sugar).

Extinction at 620 nm is monitored during the first 5 minutes at 25° C.

One Unit enzyme activity corresponds the conversion of 1 mMol mediator/min under the above assay conditions Calculation: Activity=(total volume*dE/min [U/ml]):
(ε*sample volume*1)

(ε=coefficient of extinction; $\epsilon_{620\ nm}=30[1*mmol^{-1}*cm^{-1}]$).

The assay was performed with glucose and maltose (Merck, Germany), respectively.

Results:

| Enzyme | M/G (30 mM sugar in %) | U/mg Protein. | Amino acid exchanges |
| --- | --- | --- | --- |
| WT | 105% | 800 | — |
| B/2 | 4% | 106 | N122K + S124K + Y171G + E245D + M341V + T348G + in429P |
| C/0 | 2% | 435 | Y171G + E245D + M341V + T348G + A426S + N428P + Q430M |
| C/2 | 2% | 450 | N122K + S124K + Y171G + E245D + M341V + T348G + A426S + N428P + Q430M |
| D/2 | 4% | 441 | N122K + S124K + Y171G + E245D + Q246H + M341V + T348G + T425V + N428P |

Example 9

Comparative Temperature Stability of Purified Mutants With and Without Amino Acid Exchanges N122K and S124K The purified s-GDH samples of wild-type, mutant C/0 and C/2 (Example 8) were subjected to an alternative temperature stress model which resembles production and/or transport temperature stress conditions. Solutions of 1 mg enzyme protein/20 mM potassium phosphate pH 7.0; 0.016 mg PQQ/ml were made to activate the s-GDHs. After incubation for 30 minutes at room temperature the initial activity towards glucose was determined (see Example 8) and the samples incubated in the waterbath at 48° C. After 30 minutes of temperature stress the remaining activity was measured and calculated in percent (in comparison to the initial activity).

Results:

| Enzyme | Remaining activity |
| --- | --- |
| Wilde-type | 99% |
| C/0 | 66% |
| C/2 | 94% |

The impact of the amino acid exchanges on positions N122K and S124K and the resulting improvement of temperature stability can be clearly seen, also under these alternative temperature stress conditions.

Example 10

Determination of Glucose in the Presence or Absence of Maltose

The wild-type s-GDH and variants B/2, C/2 and D/2 of s-GDH, respectively, can be applied for glucose determination in the presence or absence of maltose. The reference sample contains 50 mg glucose/dl. The "test"-samples contain 50 mg glucose/dl and 100 or 200 mg/dl maltose, respectively. Enzyme solutions with the same amounts of s-GDH activity (for example 5 U/ml; activity as determined in Example 8) are used for each assay.

In a cuvette are mixed:
1 ml 0.315 mg (4-(dimethylphosphinylmethyl)-2-methyl-pyrazolo-[1.5a]-imidazol-3-yl)-(4-nitrosophenyl)-amine ml/0.2 M citrate pH 5.8
0.033 ml Reference or Test Sample The assay is started by adding 0.050 ml of the s-GDH enzyme solution (which is an excess of s-GDH for conversion of glucose) to the cuvette. The change of absorption at 620 nm is monitored. After 2-5 minutes constant values are observed and the dE/5 min is calculated. The value obtained by measuring the reference sample with wild-type s-GDH is set to 100%. The other values are compared to this reference value and calculated in %.

Clearly less maltose interference is detected in the test samples when using the novel also more stable variants of s-GDH according to this invention.

LIST OF REFERENCES

Anthony C., Biochem. J. 320 (1996) 697-711
Anthony, C. and Ghosh, M., Current Science 72 (1997) 716-727
Anthony, C. and Ghosh, M., Prog. Biophys. Mol. Biol. 69 (1998) 1-21
Anthony, C., Biochem. Soc. Trans. 26 (1998) 413-417
Anthony, C., Adv. in Phot. and Resp. 15 (2004) 203-225
Ausubel, F., et al., in "Current protocols in molecular biology" (1994), Wiley
Cleton-Jansen, A. M., et al., Antonie Van Leeuwenhoek 56 (1989) 73-79
Cleton-Jansen, A. M., et al., J. Bacteriol. 170 (1988) 2121-2125
Cleton-Jansen, A. M., et al., Mol. Gen. Genet 217 (1989) 430-436
Davidson, V. L. in "Principles and applications of quinoproteins" (1993) the whole book, New York, Marcel Dekker
D'Costa, E. J., et al., Biosensors 2 (1986) 71-87
Dokter, P., et al., FEMS Microbiology Letters 43 (1987) 195-200
Dokter, P., et al., Biochem J. 239 (1986) 163-167
Dokter, P., et al., Biochem J. 254 (1988) 131-138
Duine, J. A. Energy generation and the glucose dehydrogenase pathway in *Acinetobacter* in "The Biology of *Acinetobacter*" (1991) 295-312, New York, Plenum Press
Duine, J. A., Biosens. Bioelectronics 10 (1995) 17-23
Duine, J. A., Eur. J. Biochem. 200 (1991) 271-284
EP 0 620 283
EP 1 167 519
EP 1 176 202
EP 1 367 120
Feng, D. F. and Doolittle, R. F., J. Mol. Evol. 25 (1987) 351-360
Frampton, J. E. and Plosker, G. L., Drugs 63 (2003) 2079-2105
Goodwin, P. M. and Anthony, C., Adv. Microbiol. Physiol. 40 (1998) 1-80
Hill, D. E., et al., Methods Enzymol. 155 (1987) 558-568
Igarashi, S., et al., Biochem. Biophys. Res. Commun. 264 (1999) 820-824
JP 11-243949-A
JP 2004173538
Kaufmann, N., et al. Development and evaluation of a new system for determining glucose from fresh capillary blood and heparinised venous blood in "Glucotrend" (1997) 1-16, Mannheim, Boehringer Mannheim GmbH
Kim, C. H. et al., Current Microbiology 47 (2003) 457-461
Laurinavicius, V., et al., Analytical Letters 32 (1999) 299-316
Laurinavicius, V., et al., Monatshefte fuer Chemie 130 (1999) 1269-1281
Laurinavicius, V. et al, Biologija (2003) 31-34
Leung, D. W., et al., Technique 1 (1989) 11-15
Malinauskas, A. et al., Sensors and Actuators, B: Chemical 100 (2004) 395-402
Matsushita, K. and Adachi, O. Bacterial quinoproteins glucose dehydrogenase and alcohol dehydrogenase in "Principles and applications of Quinoproteins" (1993) 47-63, New York, Marcel Dekker
Matsushita, K., et al., Antonie Van Leeuwenhoek 56 (1989) 63-72
Matsushita, K., et al., Biochemistry 28 (1989) 6276-6280
Matsushita, K., et al., Bioscience Biotechnology & Biochemistry 59 (1995) 1548-1555
Olsthoorn, A. J. and Duine, J. A., Arch. Biochem. Biophys. 336 (1996) 42-48
Olsthoorn, A. J. and Duine, J. A., Biochemistry 37 (1998) 13854-13861
Oubrie A., Biochim. Biophys. Acta 1647 (2003) 143-151
Oubrie, A. and Dijkstra, B. W., Protein Sci. 9 (2000) 1265-1273
Oubrie, A., et al., Embo J. 18 (1999) 5187-5194
Oubrie, A., et al., J. Mol. Biol. 289 (1999) 319-333
Oubrie, A., et al., Proc. Natl. Acad. Sci. U.S.A 96 (1999) 11787-11791
Reddy S, and Bruice, T. C., J. Am. Chem. Soc. 126 (2004) 2431-2438
Sambrook, J., et al., in "Molecular Cloning: A Laboratory Manual" (1989)-, Cold Spring Harbour, N.Y., Cold Spring Harbour Laboratory Press
U.S. Pat. No. 5,484,708
U.S. Pat. No. 5,997,817
U.S. Pat. No. 6,057,120
U.S. Pat. No. 6,103,509
Wens, R., et al., Perit. Dial. Int. 18 (1998) 603-609
WO 02/34919
WO 88/09373
Yamada, M. et al., Biochim. Biophys. Acta 1647 (2003) 185-192
Ye, L., et al., Anal. Chem. 65 (1993) 238-241

The invention claimed is:

1. An isolated mutant protein of PQQ-dependent s-GDH, said mutant having at least 89% sequence identity with the *A. calcoaceticus* s-GDH wild-type sequence (SEQ ID NO: 2) and characterized in that in at least one of the positions 122 and 124 the amino acid lysine is present, wherein these positions correspond to the amino acid positions known from the *A. calcoaceticus* s-GDH wild-type sequence (SEQ ID NO: 2).

2. The mutant of claim 1, wherein the amino acid at position 122 is a lysine.

3. The mutant of claim 1, wherein the amino acid at position 124 is a lysine.

4. The mutant of claim 1, wherein the amino acid lysine is present at both the positions 122 and 124.

5. The mutant according to claim 1 further comprising one or more amino acid substitutions, relative to the sequence of SEQ ID NO: 2, at one or more positions selected from the group consisting of positions 16, 22, 65, 76, 116, 120, 127, 143, 168, 169, 171, 177, 224, 227, 230, 231, 245, 246, 255, 277, 287, 294, 295, 299, 302, 305, 307, 308, 317, 321, 323, 341, 348, 349, 354, 355, 364, 378, 422, 425, 428 and 438.

6. The mutant according to claim 5, wherein said protein comprises an amino acid substitution at position 348 relative to the sequence of SEQ ID NO: 2.

7. The mutant according to claim 5, wherein said protein comprises an amino acid substitution at position 428 relative to the sequence of SEQ ID NO: 2.

8. The mutant according to claim 5, wherein said protein comprises an amino acid substitution at both positions 348 and 428.

9. The mutant of claim 6, wherein the native threonine at position 348 is replaced by alanine, glycine, or serine.

10. An isolated polynucleotide encoding the s-GDH mutant protein of claim 1.

11. An expression vector comprising an isolated polynucleotide as defined in claim 10 operably linked to a promoter sequence capable of promoting the expression of said polynucleotide in a host cell.

12. A host cell comprising the expression vector of claim 11.

13. A process for producing s-GDH variants comprising culturing the host cell of claim 12 under conditions suitable for production of the enzyme variants.

14. A method of detecting, determining or measuring glucose in a sample using an s-GDH mutant according to claim 1, said improvement comprising contacting the sample with the mutant.

15. The method of claim 14 further characterized in that said detection, determination or measurement of glucose is performed using a sensor or test strip device.

16. A device for the detection or measurement of glucose in a sample comprising an s-GDH mutant according to claim 1 and other reagents required for said measurement.

17. An isolated mutant protein of PQQ-dependent s-GDH comprising a sequence that differs from SEQ ID NO: 2 by 20 or less amino acid substitutions and/or insertions and includes an amino acid substitution at position 122, (relative to SEQ ID NO: 2), and optionally one or more additional amino acid substitutions, relative to the sequence of SEQ ID NO: 2, at positions selected from the group consisting of positions 16, 22, 65, 76, 116, 120, 124, 127, 143, 168, 169, 171, 177, 224, 227, 230, 231, 245, 246, 255, 277, 287, 294, 295, 299, 302, 305, 307, 308, 317, 321, 323, 341, 348, 349, 354, 355, 364, 378, 422, 425, 426, 428, 430 and 438, and an optional insertion of proline at position 429, wherein at least one of positions 122 or 124 is substituted with the amino acid lysine, wherein said mutant has at least a two-fold improved substrate specificity for glucose as compared to one other selected sugar substrate and a thermo stability that is at least 20% of the thermo stability as measured for the wild-type enzyme.

18. The mutant protein according to claim 17 wherein the amino acid at position 428 is substituted with an amino acid selected from the group consisting of leucine, proline and valine.

19. The mutant protein according to claim 17 wherein the amino acid at position 348 is substituted with an amino acid selected from the group consisting of alanine, glycine and serine.

20. The mutant protein according to claim 17 wherein both amino acids at positions 122 and 124 are substituted with the amino acid lysine, the amino acid at position 348 is substituted with an amino acid selected from the group consisting of alanine, glycine and serine, and the amino acid at position 428 is substituted with an amino acid selected from the group consisting of leucine, proline and valine.

21. The mutant protein according to claim 17 wherein said protein differs from SEQ ID NO:2 by amino acid substitutions at
a) positions 65, 122, 124, 171, 245, 341, 348, 426, 428, 430, and 436, or
b) positions 65, 122, 124, 171, 245, 341, 348, 426, 428, and 430 or
c) positions 122, 124, 171, 245, 246, 341, 348, 425, and 428.

22. The mutant protein according to claim 17 wherein said protein comprises a sequence that differs from SEQ ID NO: 2 by 20 or less amino acid substitutions and includes amino acid substitutions N122K, T348G and N428P (relative to SEQ ID NO: 2), and optionally one or more additional amino acid substitutions, relative to the sequence of SEQ ID NO: 2, selected from the group consisting of Y171G, S124K, E245D, Q246H, M341, T425V, A426S and Q430M, and an optional insertion of proline at position 429, wherein said mutant has an at least two-fold improved substrate specificity for glucose as compared to at least one other selected sugar substrate and a thermo stability that is at least 20% of the thermo stability as measured for the wild-type enzyme.

23. The mutant protein according to claim 17 wherein said protein differs from SEQ ID NO: 2 only by the following amino acid substitutions N122K+S124K+Y171G+E245D+M341V+T348G+A426S+N428P+Q430M.

* * * * *

SEQUENCE LISTING

<160> NUMBER OF SEQ ID NOS: 18

<210> SEQ ID NO 1
<211> LENGTH: 1362

```
<212> TYPE: DNA
<213> ORGANISM: Acinetobacter calcoaceticus
<220> FEATURE:
<221> NAME/KEY: CDS
<222> LOCATION: (1)..(1362)

<400> SEQUENCE: 1 gat gtt cct cta act cca tct caa ttt gct aaa gcg aaa tca gag aac      48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cac gcg ttg      96
Phe Asp Lys Lys Val Ile Leu Ser Asn Leu Asn Lys Pro His Ala Leu
                20                  25                  30 tta tgg gga cca gat aat caa att tgg tta act gag cga gca aca ggt     144
Leu Trp Gly Pro Asp Asn Gln Ile Trp Leu Thr Glu Arg Ala Thr Gly
            35                  40                  45 aag att cta aga gtt aat cca gag tcg ggt agt gta aaa aca gtt ttt     192
Lys Ile Leu Arg Val Asn Pro Glu Ser Gly Ser Val Lys Thr Val Phe
50                  55                  60 cag gta cca gag att gtc aat gat gct gat ggg cag aat ggt tta tta     240
Gln Val Pro Glu Ile Val Asn Asp Ala Asp Gly Gln Asn Gly Leu Leu
65                  70                  75                  80 ggt ttt gcc ttc cat cct gat ttt aaa aat aat cct tat atc tat att     288
Gly Phe Ala Phe His Pro Asp Phe Lys Asn Asn Pro Tyr Ile Tyr Ile
                85                  90                  95 tca ggt aca ttt aaa aat ccg aaa tct aca gat aaa gaa tta ccg aac     336
Ser Gly Thr Phe Lys Asn Pro Lys Ser Thr Asp Lys Glu Leu Pro Asn
            100                 105                 110 caa acg att att cgt cgt tat acc tat aat aaa tca aca gat acg ctc     384
Gln Thr Ile Ile Arg Arg Tyr Thr Tyr Asn Lys Ser Thr Asp Thr Leu
        115                 120                 125 gag aag cca gtc gat tta tta gca gga tta cct tca tca aaa gac cat     432
Glu Lys Pro Val Asp Leu Leu Ala Gly Leu Pro Ser Ser Lys Asp His
130                 135                 140 cag tca ggt cgt ctt gtc att ggg cca gat caa aag att tat tat acg     480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat     528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat     576
Gln Ala Gln His Thr Pro Thr Gln Gln Glu Leu Asn Gly Lys Asp Tyr
            180                 185                 190 cac acc tat atg ggt aaa gta cta cgc tta aat ctt gat gga agt att     624
His Thr Tyr Met Gly Lys Val Leu Arg Leu Asn Leu Asp Gly Ser Ile
        195                 200                 205 cca aag gat aat cca agt ttt aac ggg gtg gtt agc cat att tat aca     672
Pro Lys Asp Asn Pro Ser Phe Asn Gly Val Val Ser His Ile Tyr Thr
210                 215                 220 ctt gga cat cgt aat ccg cag ggc tta gca ttc act cca aat ggt aaa     720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc     768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa     816
Ile Val Lys Gly Gly Asn Tyr Gly Trp Pro Asn Val Ala Gly Tyr Lys
            260                 265                 270 gat gat agt ggc tat gct tat gca aat tat tca gca gca gcc aat aag     864
Asp Asp Ser Gly Tyr Ala Tyr Ala Asn Tyr Ser Ala Ala Ala Asn Lys
        275                 280                 285
```

```
tca att aag gat tta gct caa aat gga gta aaa gta gcc gca ggg gtc      912
Ser Ile Lys Asp Leu Ala Gln Asn Gly Val Lys Val Ala Ala Gly Val
    290                 295                 300 cct gtg acg aaa gaa tct gaa tgg act ggt aaa aac ttt gtc cca cca      960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca     1008
Leu Lys Thr Leu Tyr Thr Val Gln Asp Thr Tyr Asn Tyr Asn Asp Pro
        325                 330                 335 act tgt gga gag atg acc tac att tgc tgg cca aca gtt gca ccg tca     1056
Thr Cys Gly Glu Met Thr Tyr Ile Cys Trp Pro Thr Val Ala Pro Ser
    340                 345                 350 tct gcc tat gtc tat aag ggc ggt aaa aaa gca att act ggt tgg gaa     1104
Ser Ala Tyr Val Tyr Lys Gly Gly Lys Lys Ala Ile Thr Gly Trp Glu
355                 360                 365 aat aca tta ttg gtt cca tct tta aaa cgt ggt gtc att ttc cgt att     1152
Asn Thr Leu Leu Val Pro Ser Leu Lys Arg Gly Val Ile Phe Arg Ile
        370                 375                 380 aag tta gat cca act tat agc act act tat gat gac gct gta ccg atg     1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg     1248
Phe Lys Ser Asn Asn Arg Tyr Arg Asp Val Ile Ala Ser Pro Asp Gly
        405                 410                 415 aat gtc tta tat gta tta act gat act gcc gga aat gtc caa aaa gat     1296
Asn Val Leu Tyr Val Leu Thr Asp Thr Ala Gly Asn Val Gln Lys Asp
    420                 425                 430 gat ggc tca gta aca aat aca tta gaa aac cca gga tct ctc att aag     1344
Asp Gly Ser Val Thr Asn Thr Leu Glu Asn Pro Gly Ser Leu Ile Lys
        435                 440                 445 ttc acc tat aag gct aag                                             1362
Phe Thr Tyr Lys Ala Lys
    450

<210> SEQ ID NO 2
<211> LENGTH: 454
<212> TYPE: PRT
<213> ORGANISM: Acinetobacter calcoaceticus

<400> SEQUENCE: 2

Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140
```

```
Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Glu Ile Asn Leu
                245                 250                 255

Ile Val Lys Gly Gly Asn Tyr Gly Trp Pro Asn Val Ala Gly Tyr Lys
                260                 265                 270

Asp Asp Ser Gly Tyr Ala Tyr Ala Asn Tyr Ser Ala Ala Asn Lys
                275                 280                 285

Ser Ile Lys Asp Leu Ala Gln Asn Gly Val Lys Val Ala Ala Gly Val
290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
                355                 360                 365

Asn Thr Leu Leu Val Pro Ser Leu Lys Arg Gly Val Ile Phe Arg Ile
370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Asn Val Gln Lys Asp
                420                 425                 430

Asp Gly Ser Val Thr Asn Thr Leu Glu Asn Pro Gly Ser Leu Ile Lys
            435                 440                 445

Phe Thr Tyr Lys Ala Lys
    450

<210> SEQ ID NO 3
<211> LENGTH: 7
<212> TYPE: PRT
<213> ORGANISM: Artificial Sequence
<220> FEATURE:
<223> OTHER INFORMATION: sequence of s-GDH from position 120 to 126

<400> SEQUENCE: 3

Thr Tyr Asn Lys Ser Thr Asp
1               5

<210> SEQ ID NO 4
<211> LENGTH: 26
<212> TYPE: DNA
<213> ORGANISM: Artificial Sequence
```

```
<220> FEATURE:
<223> OTHER INFORMATION: Primer for m-PCR sense strand

<400> SEQUENCE: 4
cgcgcacgcg catgccgccg atgttc                                          26

<210> SEQ ID NO 5
<211> LENGTH: 23
<212> TYPE: DNA
<213> ORGANISM: Artificial Sequence
<220> FEATURE:
<223> OTHER INFORMATION: Primer for m-PCR antisense strand

<400> SEQUENCE: 5
gacggccagt gaattctttt cta                                             23

<210> SEQ ID NO 6
<211> LENGTH: 20
<212> TYPE: DNA
<213> ORGANISM: Artificial Sequence
<220> FEATURE:
<223> OTHER INFORMATION: Sequencing primer GDH 1 sense strand

<400> SEQUENCE: 6
ttaacgtgct gaacagccgg                                                 20

<210> SEQ ID NO 7
<211> LENGTH: 20
<212> TYPE: DNA
<213> ORGANISM: Artificial Sequence
<220> FEATURE:
<223> OTHER INFORMATION: Sequencing primer GDH 2 sense strand

<400> SEQUENCE: 7
atatgggtaa agtactacgc                                                 20

<210> SEQ ID NO 8
<211> LENGTH: 29
<212> TYPE: DNA
<213> ORGANISM: Artificial Sequence
<220> FEATURE:
<223> OTHER INFORMATION: Primer for wobbling at position 122 (sense
      strand)
<220> FEATURE:
<221> NAME/KEY: misc_feature
<222> LOCATION: (14)..(16)
<223> OTHER INFORMATION: n is a, c, g, or t

<400> SEQUENCE: 8
tcgttatacc tatnnnaaat caacagata                                       29

<210> SEQ ID NO 9
<211> LENGTH: 29
<212> TYPE: DNA
<213> ORGANISM: Artificial Sequence
<220> FEATURE:
<223> OTHER INFORMATION: Primer for wobbling at position 122 (antisense
      strand)
<220> FEATURE:
<221> NAME/KEY: misc_feature
<222> LOCATION: (14)..(16)
<223> OTHER INFORMATION: n is a, c, g, or t

<400> SEQUENCE: 9
tatctgttga tttnnnatag gtataacga                                       29

<210> SEQ ID NO 10
```

```
<211> LENGTH: 29
<212> TYPE: DNA
<213> ORGANISM: Artificial Sequence
<220> FEATURE:
<223> OTHER INFORMATION: Primer for wobbling at position 202 (sense
      strand)
<220> FEATURE:
<221> NAME/KEY: misc_feature
<222> LOCATION: (14)..(16)
<223> OTHER INFORMATION: n is a, c, g, or t

<400> SEQUENCE: 10
taaagtacta cgcnnnaatc ttgatggaa                                  29

<210> SEQ ID NO 11
<211> LENGTH: 29
<212> TYPE: DNA
<213> ORGANISM: Artificial Sequence
<220> FEATURE:
<223> OTHER INFORMATION: Primer for wobbling at position 202 (antisense
      strand)
<220> FEATURE:
<221> NAME/KEY: misc_feature
<222> LOCATION: (14)..(16)
<223> OTHER INFORMATION: n is a, c, g, or t

<400> SEQUENCE: 11
ttccatcaag attnnngcgt agtacttta                                  29

<210> SEQ ID NO 12
<211> LENGTH: 29
<212> TYPE: DNA
<213> ORGANISM: Artificial Sequence
<220> FEATURE:
<223> OTHER INFORMATION: Primer sequence for N122K sense strand

<400> SEQUENCE: 12
tcgttatacc tataagaaat caacagata                                  29

<210> SEQ ID NO 13
<211> LENGTH: 29
<212> TYPE: DNA
<213> ORGANISM: Artificial Sequence
<220> FEATURE:
<223> OTHER INFORMATION: Primer sequence for N122K antisense strand

<400> SEQUENCE: 13
tatctgttga tttcttatag gtataacga                                  29

<210> SEQ ID NO 14
<211> LENGTH: 27
<212> TYPE: DNA
<213> ORGANISM: Artificial Sequence
<220> FEATURE:
<223> OTHER INFORMATION: Primer sequence for N122K and S124K sense
      strand

<400> SEQUENCE: 14
cctataagaa aaagacagat acgctcg                                    27

<210> SEQ ID NO 15
<211> LENGTH: 27
<212> TYPE: DNA
<213> ORGANISM: Artificial Sequence
<220> FEATURE:
<223> OTHER INFORMATION: Primer sequence for N122K and S124K antisense
      strand

<400> SEQUENCE: 15
```

```
cgagcgtatc tgtcttttc ttatagg                                        27

<210> SEQ ID NO 16
<211> LENGTH: 4373
<212> TYPE: DNA
<213> ORGANISM: Artificial Sequence
<220> FEATURE:
<223> OTHER INFORMATION: Sequence vector pACSGDH

<400> SEQUENCE: 16
cactaactga ttacgcaccg catgtaaccg ttttcaatct gtgagtaaat tcacagttta     60
ttaacattgt gatagctatg atgacaacgt tgtcgcact  gtaactaacg tgtaacagtt    120
agttgtcagt tttgctgggg tatttcgctt ataaaaaccg ttatcacaat atcccgcgac    180
taccggacaa aaataaagag ttgaataaga gcttatccca ttagggctat tttacttgcc    240
attttggacc tgggcagtgc tcgccaaaac gcgttagcgt tttgaacgcg ctagcggcgg    300
cccgaagggc gagcgtagcg agtcaaacct cacgtactac gtgtacgctc cggttttgc     360 gcgctgtccg tgtccaaact gctgcgccaa taacgcctgg tgggataggc tctaaatacg    420
cttcggcgtt cagtaacacg cgttaacgtg ctgaacagcc gggcattttt ttacgctata    480
ccctacataa taaaaccgga gctaccatga ataagaaggt actgacccct tctgccgtga    540
tggcaagtct gttattcggc gcgcacgcgc atgccgccga tgttcctcta actccatctc    600
aatttgctaa agcgaaatca gagaactttg acaagaaagt tattctatct aatctaaata    660
agccgcacgc gttgttatgg ggaccagata atcaaatttg ttaactgag cgagcaacag     720 gtaagattct aagagttaat ccagagtcgg gtagtgtaaa aacagttttt caggtaccag    780
agattgtcaa tgatgctgat gggcagaatg gtttattagg ttttgccttc catcctgatt    840
ttaaaaataa tccttatatc tatatttcag gtacatttaa aaatccgaaa tctacagata    900
aagaattacc gaaccaaacg attattcgtc gttatacca  taataaatca acagatacgc    960
tcgagaagcc agtcgattta ttagcaggat taccttcatc aaaagaccat cagtcaggtc   1020
gtcttgtcat tgggccagat caaaagattt attatcgat  tggtgaccaa gggcgtaacc   1080
agcttgctta tttgttcttg ccaaatcaag cacaacatac gccaactcaa caagaactga   1140
atggtaaaga ctatcacacc tatatgggta agtactacg  cttaaatctt gatgaagta    1200 ttccaaagga taatccaagt tttaacgggg tggttagcca tatttataca cttggacatc   1260
gtaatccgca gggcttagca ttcactccaa atggtaaatt attgcagtct gaacaaggcc   1320
caaactctga cgatgaaatt aacctcattg tcaaggtgg  caattatggt tggccgaatg   1380
tagcaggtta taaagatgat agtggctatg cttatgcaaa ttattcagca gcagccaata   1440
agtcaattaa ggatttagct caaaatggag taaaagtagc cgcagggtc  cctgtgacga   1500 aagaatctga atggactggt aaaaacttg  tcccaccatt aaaaacttta tataccgttc   1560 aagatacccta caactataac gatccaactt gtggagagat gacctacatt tgctggccaa   1620
cagttgcacc gtcatctgcc tatgtctata agggcggtaa aaaagcaatt actggttggg   1680
aaaatacatt attggttcca tctttaaaac gtggtgtcat tttccgtatt aagttagatc   1740 caactttatag cactacttat gatgacgctg taccgatgtt aagagcaac  accgttatc    1800 gtgatgtgat tgcaagtcca gatgggaatg tcttatatgt attaactgat actgccgaa    1860 atgtccaaaa agatgatggc tcagtaacaa atacattaga aaacccagga tctctcatta   1920
agttcaccta aaggctaag  taatacagtc gcattaaaaa accgatctat aaagatcggt   1980
```

```
tttttttagtt ttagaaaaga attcactggc cgtcgtttta caacgtcgtg actgggaaaa    2040
ccctggcgtt acccaactta atcgccttgc agcacatccc cctttcgcca gctggcgtaa    2100
tagcgaagag gcccgcaccg atcgcccttc ccaacagttg cgcagcctga atggcgaatg    2160
gcgcctgatg cggtatttc tccttacgca tctgtgcggt atttcacacc gcatatggtg    2220
cactctcagt acaatctgct ctgatgccgc atagttaagc cagccccgac acccgccaac    2280
acccgctgac gcgccctgac gggcttgtct gctcccggca tccgcttaca gacaagctgt    2340
gaccgtctcc gggagctgca tgtgtcagag gttttcaccg tcatcaccga aacgcgcgag    2400
acgaaagggc ctcgtgatac gcctattttt ataggttaat gtcatgataa taatggtttc    2460
ttagacgtca ggtggcactt ttcggggaaa tgtgcgcgga accccttatttt gtttattttt    2520
ctaaatacat tcaaatatgt atccgctcat gagacaataa ccctgataaa tgcttcaata    2580
atattgaaaa aggaagagta tgagtattca acatttccgt gtcgccctta ttccctttt    2640
tgcggcattt tgccttcctg tttttgctca cccagaaacg ctggtgaaag taaaagatgc    2700
tgaagatcag ttgggtgcac gagtgggtta catcgaactg gatctcaaca gcggtaagat    2760
ccttgagagt tttcgccccg aagaacgttt tccaatgatg agcactttta aagttctgct    2820
atgtggcgcg gtattatccc gtattgacgc cgggcaagag caactcggtc gccgcataca    2880
ctattctcag aatgacttgg ttgagtactc accagtcaca gaaaagcatc ttacggatgg    2940
catgacagta agagaattat gcagtgctgc cataaccatg agtgataaca ctgcggccaa    3000
cttacttctg acaacgatcg gaggaccgaa ggagctaacc gcttttttgc acaacatggg    3060
ggatcatgta actcgccttg atcgttggga accggagctg aatgaagcca taccaaacga    3120
cgagcgtgac accacgatgc ctgtagcaat ggcaacaacg ttgcgcaaac tattaactgg    3180
cgaactactt actctagctt cccggcaaca attaatagac tggatggagg cggataaagt    3240
tgcaggacca cttctgcgct cggcccttcc ggctggctgg tttattgctg ataaatctgg    3300
agccggtgag cgtgggtctc gcggtatcat tgcagcactg gggccagatg gtaagccctc    3360
ccgtatcgta gttatctaca cgacggggag tcaggcaact atggatgaac gaaatagaca    3420
gatcgctgag ataggtgcct cactgattaa gcattggtaa ctgtcagacc aagtttactc    3480
atatatactt tagattgatt taaaacttca ttttttaattt aaaaggatct aggtgaagat    3540
cctttttgat aatctcatga ccaaaatccc ttaacgtgag ttttcgttcc actgagcgtc    3600
agacccgta gaaagatca aggatcttc ttgagatcct ttttttctgc gcgtaatctg    3660
ctgcttgcaa acaaaaaaac caccgctacc agcggtggtt tgtttgccgg atcaagagct    3720
accaactctt tttccgaagg taactggctt cagcagagcg cagataccaa atactgtcct    3780
tctagtgtag ccgtagttag gccaccactt caagaactct gtagcaccgc ctacatacct    3840
cgctctgcta atcctgttac cagtggctgc tgccagtggc gataagtcgt gtcttaccgg    3900
gttggactca agacgatagt taccggataa ggcgcagcgg tcgggctgaa cggggggttc    3960
gtgcacacag cccagcttgg agcgaacgac ctacaccgaa ctgagatacc tacagcgtga    4020
gctatgagaa agcgccacgc ttcccgaagg gagaaaggcg gacaggtatc cggtaagcgg    4080
cagggtcgga acaggagagc gcacgaggga gcttccaggg ggaaacgcct ggtatcttta    4140
tagtcctgtc gggtttcgcc acctctgact tgagcgtcga tttttgtgat gctcgtcagg    4200
ggggcggagc ctatggaaaa acgccagcaa cgcggccttt ttacggttcc tggccttttg    4260
ctggcctttt gctcacatgt tctttcctgc gttatcccct gattctgtgg ataaccgtat    4320
taccgccttt gagtgagctg ataccgctcg ccgcagccga acgacgggc ccg           4373
```

<210> SEQ ID NO 17
<211> LENGTH: 7
<212> TYPE: PRT
<213> ORGANISM: Artificial Sequence
<220> FEATURE:
<223> OTHER INFORMATION: modified amino acid sequence of s-GDH from position 120 to 126
<220> FEATURE:
<221> NAME/KEY: MISC_FEATURE
<222> LOCATION: (3)..(3)
<223> OTHER INFORMATION: Xaa at position 3 is Asn or Lys
<220> FEATURE:
<221> NAME/KEY: MISC_FEATURE
<222> LOCATION: (5)..(5)
<223> OTHER INFORMATION: Xaa at position 5 is Ser or Lys

<400> SEQUENCE: 17

Thr Tyr Xaa Lys Xaa Thr Asp
1               5

<210> SEQ ID NO 18
<211> LENGTH: 455
<212> TYPE: PRT
<213> ORGANISM: Acinetobacter baumannii

<400> SEQUENCE: 18

Asp Ile Pro Leu Thr Pro Ala Gln Phe Ala Lys Ala Lys Thr Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Val Ser Gly Ser Ala Lys Thr Val Phe
50                  55                  60

Gln Val Pro Glu Ile Val Ser Asp Ala Asp Gly Gln Asn Gly Leu Leu
65                  70                  75                  80

Gly Phe Ala Phe His Pro Asp Phe Lys His Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Thr Thr Asp Thr Phe
        115                 120                 125

Glu Lys Pro Ile Asp Leu Ile Ala Gly Leu Pro Ser Ser Lys Asp His
130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Ser Asn
                165                 170                 175

Gln Ala Gln His Thr Pro Thr Gln Gln Glu Leu Asn Ser Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
210                 215                 220

Leu Gly His Arg Asn Pro Gln Gly Leu Ala Phe Ala Pro Asn Gly Lys
225                 230                 235                 240

Leu Leu Gln Ser Glu Gln Gly Pro Asn Ser Asp Asp Glu Ile Asn Leu
                245                 250                 255

-continued

```
Val Leu Lys Gly Gly Asn Tyr Gly Trp Pro Asn Val Ala Gly Tyr Lys
            260             265             270

Asp Asp Ser Gly Tyr Ala Tyr Ala Asn Tyr Ser Ala Ala Thr Asn Lys
        275             280             285

Ser Gln Ile Lys Asp Leu Ala Gln Asn Gly Ile Lys Val Ala Thr Gly
    290             295             300

Val Pro Val Thr Lys Glu Ser Glu Trp Thr Gly Lys Asn Phe Val Pro
305             310             315             320

Pro Leu Lys Thr Leu Tyr Thr Val Gln Asp Thr Tyr Asn Tyr Asn Asp
            325             330             335

Pro Thr Cys Gly Glu Met Ala Tyr Ile Cys Trp Pro Thr Val Ala Pro
            340             345             350

Ser Ser Ala Tyr Val Tyr Thr Gly Gly Lys Lys Ala Ile Pro Gly Trp
        355             360             365

Glu Asn Thr Leu Leu Val Pro Ser Leu Lys Arg Gly Val Ile Phe Arg
    370             375             380

Ile Lys Leu Asp Pro Thr Tyr Ser Thr Thr Leu Asp Asp Ala Ile Pro
385             390             395             400

Met Phe Lys Ser Asn Asn Arg Tyr Arg Asp Val Ile Ala Ser Pro Glu
            405             410             415

Gly Asn Thr Leu Tyr Val Leu Thr Asp Thr Ala Gly Asn Val Gln Lys
            420             425             430

Asp Asp Gly Ser Val Thr His Thr Leu Glu Asn Pro Gly Ser Leu Ile
        435             440             445

Lys Phe Thr Tyr Asn Gly Lys
    450             455
```